US009260760B2

(12) United States Patent
Lin

(10) Patent No.: US 9,260,760 B2
(45) Date of Patent: Feb. 16, 2016

(54) METHOD FOR DETERMINING COMPLETE RESPONSE TO ANTICANCER THERAPY

(71) Applicant: Board of Regents, The University of Texas System, Austin, TX (US)

(72) Inventor: Edward H. Lin, Seattle, WA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/398,086

(22) PCT Filed: May 1, 2013

(86) PCT No.: PCT/US2013/039115
§ 371 (c)(1),
(2) Date: Oct. 30, 2014

(87) PCT Pub. No.: WO2013/166186
PCT Pub. Date: Nov. 7, 2013

(65) Prior Publication Data
US 2015/0152504 A1 Jun. 4, 2015

Related U.S. Application Data

(60) Provisional application No. 61/640,789, filed on May 1, 2012.

(51) Int. Cl.
*C12Q 1/68* (2006.01)
*G01N 33/574* (2006.01)

(52) U.S. Cl.
CPC ........ *C12Q 1/6886* (2013.01); *G01N 33/57419* (2013.01); *C12Q 2600/106* (2013.01); *C12Q 2600/118* (2013.01); *C12Q 2600/158* (2013.01); *G01N 2333/70596* (2013.01); *G01N 2800/52* (2013.01)

(58) Field of Classification Search
CPC ........... C12Q 1/6886; C12Q 2600/158; C12Q 2600/106; G01N 2333/70596
USPC ........................................................ 514/406
See application file for complete search history.

(56) References Cited

U.S. PATENT DOCUMENTS

| 8,044,033 | B2 | 10/2011 | Lin |
| 2005/0227929 | A1 | 10/2005 | Masferrer |
| 2009/0156548 | A1 | 6/2009 | Lin |
| 2012/0100997 | A1 | 4/2012 | Lenz |

OTHER PUBLICATIONS

Cianchi et al., "Up-regulation of cyclooxygenase 2 gene expression correlates with tumor angiogenesis in human colorectal cancer," *Gastroenterology*, 121(6):1339-1347, 2001.
Iinuma et al., "Clinical significance of circulating tumor cells, including caner stem-like cells, in peripheral blood for recurrence and prognosis in patients with Dukes' stage B and C colorectal cancer," *Journal of Clinical Oncology*, 29(12):1547-1555, 2011.
Lin et al., "A phase II study of capecitabine and concomitant boost radiotherapy (XRT) in patients (pts) with locally advanced rectal cancer (LARC)," *Proc. Am. Soc. Clin. Oncol.*, 23:269, 2005.
Lin et al., "Elevated circulating endothelial progenitor marker CD133 messenger RNA levels predict colon cancer recurrence," *Cancer*, 110:534-542, 2007.
Lin et al., "Elevated stem cell marker CD133 mRNA in peripheral blood predicts colon cancer recurrence," *Journal of Clinical Oncology*, 2007 ASCO Annual Meeting Proceedings Part 1, 25(18S), Abstract No. 10504, 2007.
Lyden et al., "Impaired recruitment of bone-marrow-derived endothelial and hematopoietic precursor cells blocks tumor angiogenesis and growth," *Nat. Med.*, 7(11):1194-1201, 2001.
Mancuso et al., "Strategies to investigate circulating endothelial cells in cancer," *Pathophysiol. Haemost. Thromb.*, 33:503-506, 2003.
Milas, "Cyclooxygenase-2 (COX-2) enzyme inhibitors and radiotherapy: preclinical basis," *Am. J. Clin. Oncol.*, 26(4):S66-S69, 2003.
Ong et al., "CD133 expression predicts for non-response to chemotherapy in colorectal cancer," *Modern Pathology*, 23:450-457, 2010.
PCT International Preliminary Report on Patentability issued in International Application No. PCT/US2013/039115, mailed Nov. 13, 2014.
PCT International Search Report and Written Opinion issued in International Application No. PCT/US2013/039115, mailed Jul. 25, 2013.
Sussman et al., "Blood markers for vasculogenesis increase with tumor progression in patients with breast carcinoma," *Cancer Biol. Therapy*, 2:255-256, 2003.
Werner et al., "Circulating endothelial progenitor cells and cardiovascular outcomes," *N. Engl. J. Med.*, 353:999-1007, 2005.
Willett et al., "Direct evidence that the VEGF-specific antibody bevacizumab has antivascular effects in human rectal cancer," *Nat. Med.*, 10:145-147, 2004.
Yu et al., "CD133, Stem Cells, and Cancer Stem Cells: Myth or Reality?" *Curr. Colorectal Cancer Rep*, 7: 253-259, 2011.

*Primary Examiner* — Kristin Vajda
(74) *Attorney, Agent, or Firm* — Parker Highlander PLLC

(57) ABSTRACT

Methods for identifying patients with molecular or complete remission of colorectal cancer following therapy a fluorocytidine derivative and a COX-2 enzyme inhibitor by quantifying CD 133 expression levels. Methods for detecting cancer stem cells by quantifying serum CD 133 RNA levels are also provided.

17 Claims, 11 Drawing Sheets

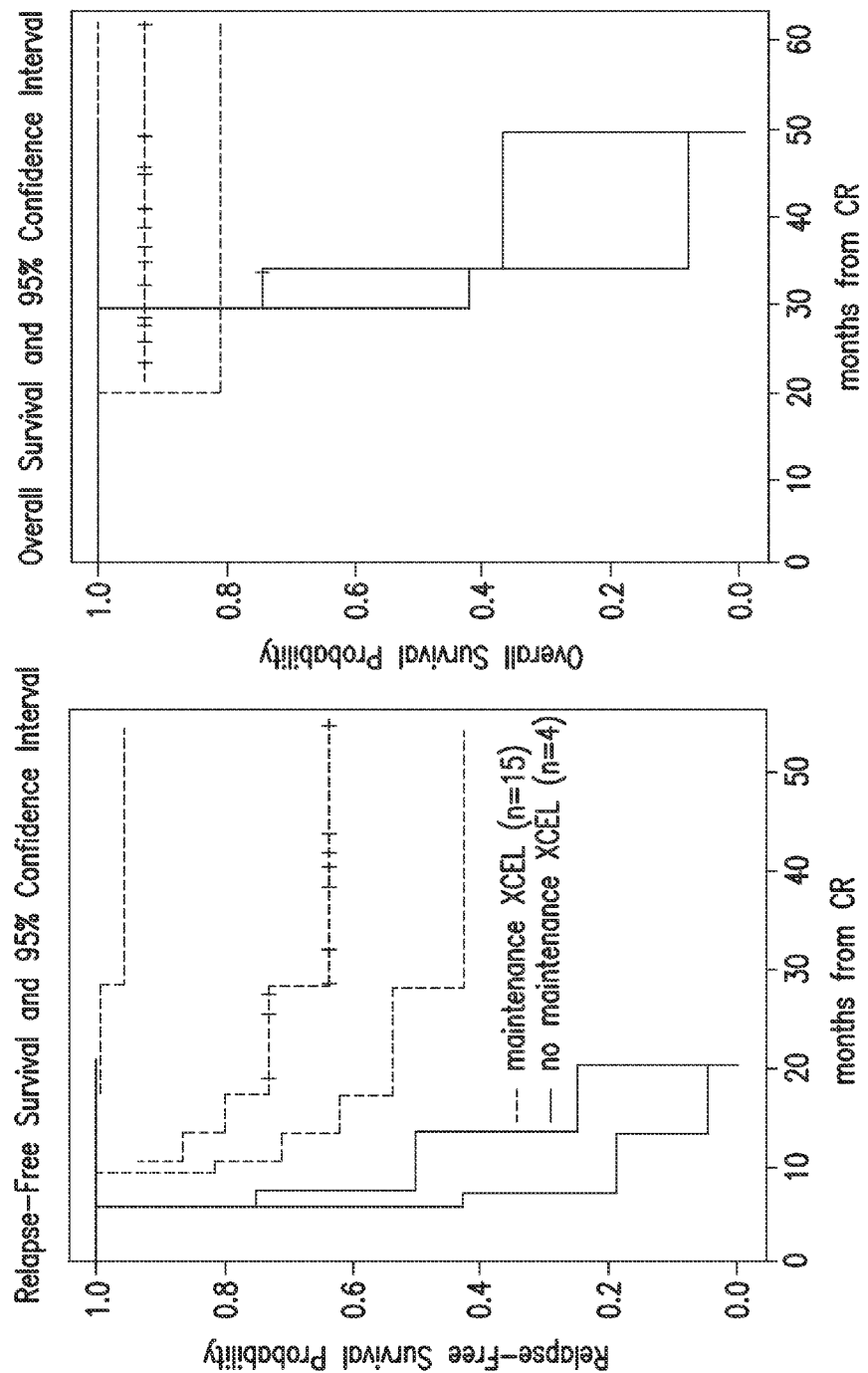

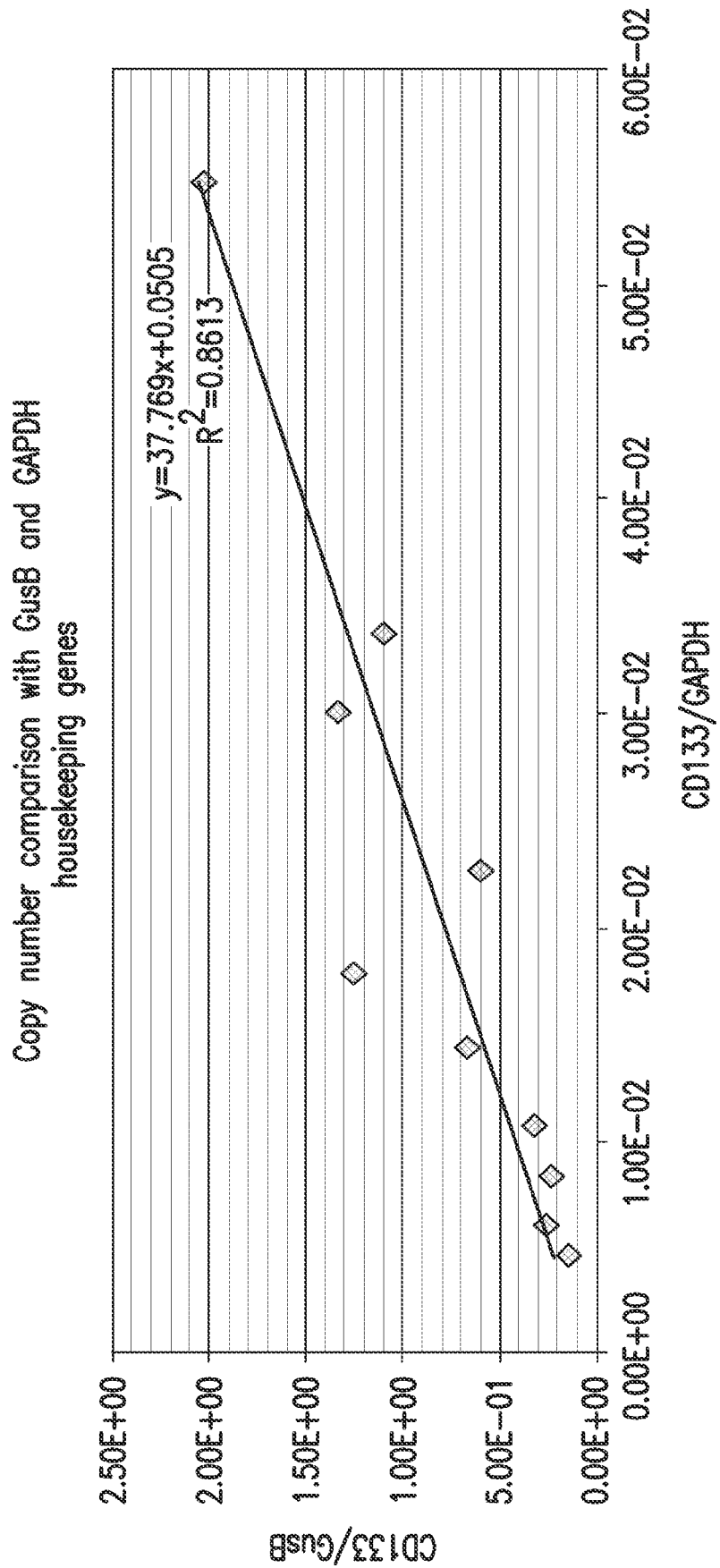

METHOD FOR DETERMINING COMPLETE RESPONSE TO ANTICANCER THERAPY

This application is a national phase application under 35 U.S.C. §371 of International Application No. PCT/US2013/039115, filed May 1, 2013, which claims the benefit of U.S. Provisional Patent Application No. 61/640,789, filed May 1, 2012, the entirety of each of which is incorporated herein by reference.

BACKGROUND OF THE INVENTION

This application is related to U.S. Pat. No. 8,044,033, issued Oct. 25, 2011, the entirety of which is incorporated herein by reference.

1. Field of the Invention

The present invention relates generally to the field of molecular biology and oncology. More particularly, it concerns methods for detecting cancer stem cells and for determining a response to anti-cancer therapy.

2. Description of Related Art

Colorectal cancer is the second most common cause of cancer-related death in the United States (Jemal et al., 2005). The benchmark median overall survival of patients receiving first-line and second-line combination chemotherapy for metastatic colorectal cancer is currently 17-20 months and 10-12 months, respectively (Douillard et al., 2000; Goldberg et al., 2004; Tournigand et al., 2004; Rothenberg et al., 2003; Hurwitz et al., 2004; Giantonio et al., 2005; Cunningham et al., 2004; Diaz Rubio et al., 2005). Unfortunately, the five year overall survival was merely 5-8%.

Various combination therapies have been used to address this form of cancer. Combining bevacizumab or cetuximab with cytotoxic chemotherapy produced response rate to 60-80%, converting more patients to be surgically resectable, but not overall complete response (CR) rate ranging between 2-10% (Hurwitz et al., 2004; Diaz Rubio et al., 2005; Hochster, 2006). However, little is known about natural history of the 2-10% CR patients from chemotherapy, as majority do relapse within two years. The natural history of these surgical CR patients may be the closest approximation to that of the CR patients rendered by chemotherapy.

In xenograft models, adding celecoxib (XCEL) (CELEBREX®; Pfizer, New York, N.Y.) a selective COX-2 inhibitor, to chemotherapy or radiation therapy significantly increased antitumor efficacy compared to either treatment modality alone (Cianchi et al., 2001; Masferrer et al., 2000; Sheng et al., 1998; Milas, 2003). More recently it was shown in a study of 66 patients with metastatic colorectal cancer who underwent XCEL (in combination with capecitabine)+/−radiation therapy experienced reduced toxicities and that nineteen (29%) of sixty-six patients unexpectedly achieved CR with XCEL alone (n=9) or with radiation (n=12), see e.g., U.S. Pat. No. 8,044,033. However, there remains no method to predict which patient have achieved CR following such therapy or to determine whether residual cancer stem cells remain in patients.

SUMMARY OF THE INVENTION

In a first embodiment there is provided a method for treating a subject comprising (a) selecting a subject that has received or is receiving an anticancer therapy to treat colorectal cancer comprising administration of a fluorocytidine derivative and a cyclooxygenase-2 (COX-2) enzyme inhibitor and determined to have an elevated level of CD133 expression; and (b) administering a further anticancer therapy to the subject. For example, in certain aspects, a subject is determined to have an elevated level CD133 expression in the blood. In some aspects the elevated CD133 expression is elevated of CD133 RNA or protein expression. For example, a subject may be determined to have a CD133 RNA expression level greater than about 0.56, 0.6, 0.7, 0.8, 0.9, 1.0, 1.5, 2.0, 2.5, 3.0, 3.5., 4.0, 4.5, 5.0, 5.5, 6.0, 6.5, or 7.0, when normalized to GAPDH RNA level (e.g., an expression level between 0.56 and 7.0). As used herein, CD133 RNA expression level is expressed as the quantity of CD133 mRNA relative to a GAPDH mRNA control (see, e.g., Iinuma et al., 2011, the entirety of which is incorporated herein by reference). A skilled artisan will recognize that CD133 levels can also be normalized to any other control gene expression level (e.g., a housekeeping gene) and while the raw numerical values would differ, the same information could be derived from the assessment. In still further aspects, a subject determined to have an elevated CD133 expression level is determined to have an expression level greater than that of a cancer-free control subject. For example, the elevated level of CD133 can be a serum CD133 RNA level that is between about 2, 4, 6, 8 and 10, 20 or 30 times greater than the CD133 expression level in a sample from the cancer-free control subject (e.g., less than about 10 times greater than the level a control subject).

In still a further aspect a method of the embodiments further comprises selecting a subject for a further anticancer therapy that was determine to have an elevated expression (e.g., mRNA expression) of carcinoembryonic antigen (CEA), CD133, cytokeratin (CK) 19 and/or CK20 relative to a control level.

Thus, in a further embodiment there is provided a method for treating a subject comprising (a) selecting a subject that has received or is receiving an anticancer therapy to treat colorectal cancer comprising administration of a fluorocytidine derivative and a COX-2 enzyme inhibitor and determined to have a CD133 RNA expression level (e.g., in the blood) (i) greater than about 0.56, when normalized to GAPDH RNA level, (e.g., such as between 0.56 and 7.0 or greater) or (ii) greater than the CD133 RNA expression level in a sample from a cancer-free control (e.g., between about 2 and 10 times greater than a control subject); and (b) administering a further anticancer therapy to the subject.

In still a further embodiment there is provided a method of detecting cancer stem cells (or detecting a risk for the presence of cancer stem cells) in a subject comprising determining CD133 expression in a biological sample of a subject who has undergone or is undergoing an anticancer therapy to treat colorectal cancer comprising administration of a fluorocytidine derivative and a COX-2 enzyme inhibitor, wherein an elevated CD133 expression level indicates the presence of (or a risk for the presence of) cancer stem cells in the subject. In some aspects, the elevated CD133 expression is an elevated protein or RNA expression level. For example, a method of the embodiments can comprise determining a CD133 RNA expression level, wherein an RNA expression level greater than about 0.56 (when normalized to GAPDH RNA level) or between about 0.56 and 7.0 or greater indicates the presence of cancer stem cells in the subject. In some aspects, a CD133 RNA expression level of between about 0.56 and 7.0 or between about 0.56 and 6.0, 5.5, 4.0, 3.5, 3.0, 2.5, 2.0, 1.5 or 1.0 indicates the presence of cancer stem cells in the subject. In still further aspects, a method comprises determining whether a subject has a serum CD133 RNA level greater than that of a cancer-free control subject (e.g., between about 2 and 10 times greater) to identify a subject having, at risk of having or having a biomarker of cancer stem cells. In still further aspects, a method of the embodiments further comprises determining the expression (e.g., mRNA expression) of CEA, CK19 and/or CK20 in the subject, wherein elevated expression of CEA, CK19 and/or CK20 relative to a control level indicates the presence or an increased risk for the presence of cancer stem cells in the subject.

In a further aspect there is provided a method of detecting a biomarker of cancer stem cells in a subject comprising (a) determining CD133 RNA expression in a biological sample of a subject who has undergone or is undergoing an anticancer therapy to treat colorectal cancer comprising administration of a fluorocytidine derivative and a COX-2 enzyme inhibitor; and (b) identifying the subject as having a biomarker of cancer stem cells if (i) the CD133 RNA expression level in the sample is greater than about 0.56; or (ii) greater than the CD133 RNA expression level in a sample from a cancer-free control.

In still a further embodiment there is provided a method for detecting a biomarker of cancer stem cells in a subject comprising determining CD133 expression in a biological sample of a subject who has undergone or is undergoing an anticancer therapy to treat colorectal cancer comprising administration of a fluorocytidine derivative and a COX-2 enzyme inhibitor, wherein an elevated CD133 expression level indicates the presence of a biomarker for cancer stem cells in the subject. In certain aspects, a method further comprises identifying the subject as not having a biomarker of cancer stem cells if the CD133 RNA expression level in the sample is less than about 0.56 or less than the CD133 expression level in a sample from a cancer-free control. For example, in certain aspects, identifying the subject as not having or not having a biomarker of cancer stem cells comprises reporting (e.g., in an electronic or written report) that the subject has (or does not have) a biomarker of cancer stem cells.

In yet a further embodiment there is provided a method of determining whether a subject is in need of further anticancer therapy comprising, determining CD133 expression in a biological sample of a subject who has undergone or is undergoing an anticancer therapy to treat colorectal cancer comprising administration of a fluorocytidine derivative and a COX-2 enzyme inhibitor, wherein an elevated CD133 expression level indicates the need for further anticancer therapy in the subject. In some aspects, the elevated CD133 expression is an elevated protein or RNA expression level. For example, a method of the embodiments can comprise determining a CD133 RNA expression level, wherein an RNA expression level greater than about 0.56 or between about 0.56 and 7.0 or greater indicates the need for further anticancer therapy in the subject. In some aspects, an elevated CD133 expression level is greater than the CD133 RNA expression level in a sample from a cancer-free control (e.g., between 2 and 10 times greater). In still further aspects, a method of the embodiments further comprises determining the expression (such as the mRNA expression) of a further biomarker gene such as CEA, CK19 and/or CK20 in the subject, wherein elevated expression of CEA, CK19 and/or CK20 indicates that the subject is in need of a further anticancer therapy.

In still a further embodiment a method is provided for determining whether a subject is in need of further anticancer therapy comprising (a) determining CD133 RNA expression in a biological sample of a subject who has undergone or is undergoing an anticancer therapy to treat colorectal cancer comprising administration of a fluorocytidine derivative and a COX-2 enzyme inhibitor; and (b) identifying the subject as in need of further anticancer therapy if the CD133 RNA expression level in the sample is greater than about 0.56 or greater than the CD133 expression level in a sample from a cancer-free control. In further aspects, a method comprises identifying the subject as not in need of further anticancer therapy if the CD133 RNA expression level in the sample is less than about 0.56 or less than the CD133 expression level in a sample from a cancer-free control. For example, in certain aspects, identifying the subject as in need of (or not in need of) a further anticancer therapy comprises reporting (e.g., in an electronic or written report) that the subject is in need of (or is not in need of) a further anticancer therapy.

In a related embodiment a method is provided for determining a complete response to an anti-cancer therapy in a subject comprising: (a) determining CD133 RNA expression in a biological sample of a subject who has undergone or is undergoing an anticancer therapy to treat colorectal cancer comprising administration of a fluorocytidine derivative and a COX-2 enzyme inhibitor; and (b) identifying the subject as having a complete response to the anticancer therapy if the CD133 RNA expression level in the sample is (i) less than about 0.56, when normalized to GAPDH RNA level, or (ii) less than the CD133 RNA expression level in a sample from a cancer-free control.

In certain aspects, selecting a subject determined to have an elevated level of CD133, CEA, CK19 and/or CK20 expression comprises measuring CD133, CEA, CK19 and/or CK20 expression in the subject (e.g., in a sample from the subject). In further aspects, selecting a subject can comprise obtaining a report, such as written or electronic report, that provides a CD133, CEA, CK19 and/or CK20 expression level for the subject.

In certain aspects, a method of the embodiments comprises determining a CD133, CEA, CK19 and/or CK20 expression level in a subject. In some aspects, the level of CD133, CEA, CK19 and/or CK20 protein expression is determined. Methods that can be employed to determine such protein expression include, but are not limited to, mass spectroscopy, an aptamer binding assay or an immune-detection method that employs an antibody (e.g., Western blot, ELISA or IHC). In further aspects, determining a CD133, CEA, CK19 and/or CK20 expression level comprises determining a RNA expression level. Methods that can be employed to determine an RNA expression level include, but are not limited to, nucleic acid hybridization (e.g., Northern blot or hybridization to an array), nucleic acid sequencing or reverse transcription polymerase chain reaction (RT-PCR). In further aspects, a method of the embodiments further comprises reporting a CD133 expression level for a subject (e.g., in a written or electronic report). In still further aspects, a method of the embodiments comprises reporting a CD133, CEA, CK19 and/or CK20 expression level for a subject; reporting whether a subject comprises cancer stem cells; or reporting whether a subject has a complete response to an anticancer therapy.

In still further aspects, a method of the embodiments comprises determining or obtaining the expression level of at least a second gene in a subject in addition to CD133. In some cases, the second gene is a gene expressed in cancer cells or in cancer stem cells. In further aspects, the second gene is a reference gene. Certain aspects of the embodiments concern determining or obtaining a CD133 RNA expression level for a subject (or in a sample from a subject). In certain aspects, the CD133 RNA expression level is a relative expression level as compared to the expression of a reference RNA. For example, in some cases the reference RNA can be an RNA encoding glyceraldehyde-3-phosphate dehydrogenase (GAPDH), see e.g., NCBI accession no. NM_002046, incorporated herein by reference. Likewise, expression of additional biomarker genes, such as CEA, CK19 and/or CK20 can be determined relative to the expression of a reference gene such as GAPDH.

Certain aspects of the embodiments concern subjects that are determined to have elevated CD133 expression. In some aspects the elevated CD133 expression is elevated expression in a whole blood, serum or a tissue sample from the subject. In some aspects, a method of the embodiments can comprise obtaining a biological sample from a subject. It will be recognized that a sample may be directly obtained from a subject (e.g., by drawing blood from a subject) or may be obtained by a third party (e.g., a doctor or laboratory). In certain aspects, a biological sample can be a blood, serum, fecal or tissue sample. In certain aspects, methods of the embodiments involve assessing, obtaining or comparing CD133 levels in a sample from a cancer-free control subject. In some aspects, a cancer-free subject is a subject that has never had a cancer and never received an anticancer therapy. In still further aspects, the control subject is an age-matched control, such as a control that has an age with-in 10, 5 or 2 years of the subject being assessed.

Aspects of the embodiments concern a subject that has or is receiving an anticancer therapy comprising administration of a fluorocytidine derivative, a COX-2 enzyme inhibitor and, optionally, a further anticancer therapy. In some specific aspects, a subject has or is receiving an anticancer therapy comprising administration of celecoxib and capecitabine. In certain aspects, the subject has or is receiving an anticancer therapy comprising administration of a fluorocytidine derivative, a COX-2 enzyme inhibitor and radiation therapy. In yet further aspects, a subject has or is receiving an anticancer therapy comprising administration of celecoxib, capecitabine and radiation.

In certain aspects, a subject of the embodiments is a canine, feline, equine, bovine or human subject. In some aspects, the subject is diagnosed with or was previously diagnosed with colorectal cancer (e.g., metastatic colorectal cancer). In further aspects, the subject is being treated or was previously treated for colorectal cancer. For example, the colorectal cancer can be a metastatic colorectal cancer, such as a cancer comprising nodal metastases (e.g., solitary or clustered nodal metastases). In some aspects, a subject of the embodiments may be further defined as a subject that has or has previously had capecitabine-induced hand-foot syndrome (HFS).

In still further aspects, a subject of the embodiments is a subject that does not comprise an elevated CD133 expression level, such as an elevated CD133 RNA expression level. Accordingly, certain aspects of the embodiments can comprise reporting that a subject does not comprise cancer stem cells; or reporting that as subject has a complete response to an anticancer therapy.

Aspects of the embodiments concern anticancer therapies involving a COX-2 enzyme inhibitor. In certain aspects, the COX-2 enzyme inhibitor is a selective COX-2 inhibitor. For example, In some aspects, the COX-2 selective enzyme inhibitor may be meloxicam, valdecoxib (Bextra™), celecoxib (Celebrex™), rofecoxib (Vioxx™) or naproxen (Aleve™). While in a preferred embodiment the COX-2 inhibitor is celecoxib, it is contemplated that a COX-2 inhibitor other than celecoxib is included as an embodiment of the invention. In certain cases, the dose of celecoxib administered to a subject may be defined as less than about 200 mg b.i.d, more than 200 mg b.i.d or about 200 mg b.i.d.

In certain aspects, the embodiments concern anticancer therapies involving a fluorocytidine derivative. For example, a fluorocytidine derivative can be a derivative a 5'-deoxy-5-fluorocytidine derivative or a derivative described in U.S. Pat. No. 4,966,891, incorporated herein by reference. In certain aspects, the fluorocytidine derivative is capecitabine. In certain aspects the capecitabine is administered orally. For example, the capecitabine may be administered in a dose of from about 850 to about 1300 mg/m²/d, from about 900 to about 1250 mg/m²/d or a dose of about 1000 mg/m²/d.

Certain aspects of the embodiments concern administering a further anticancer therapy to a subject (e.g., a subject determined to have an elevated CD133 expression level). In some aspects, the further anticancer therapy comprises radiation therapy, chemotherapy, immunotherapy or surgery. In certain aspects, the further anticancer therapy is a radiation therapy. Such a radiation therapy may involve, for example, administration of from about 25 to about 65 Gy, from about 35 to about 50 Gy or from about 35 to about 45 Gy of radiation to the subject. Furthermore, in certain cases, the radiation therapy comprises a 3-D conformal planning technique. In some aspects, the further anticancer therapy comprises treatment with a fluorocytidine derivative, a COX-2 enzyme inhibitor, and optionally a radiation therapy.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10A-B: RFS (FIG. 10A) and OS (FIG. 10B) with maintenance versus no maintenance XCEL (study 3).

FIG. 11: Comparison of CD133 mRNA copy number results when normalized to the GusB and GAPDH housekeeping genes. Results show that normalization to either GusB or GAPDH provide similar results, indicating that any equivalent housekeeping gene could be used for such normalization.

DESCRIPTION OF ILLUSTRATIVE EMBODIMENTS

I. The Present Invention

Figure 1:
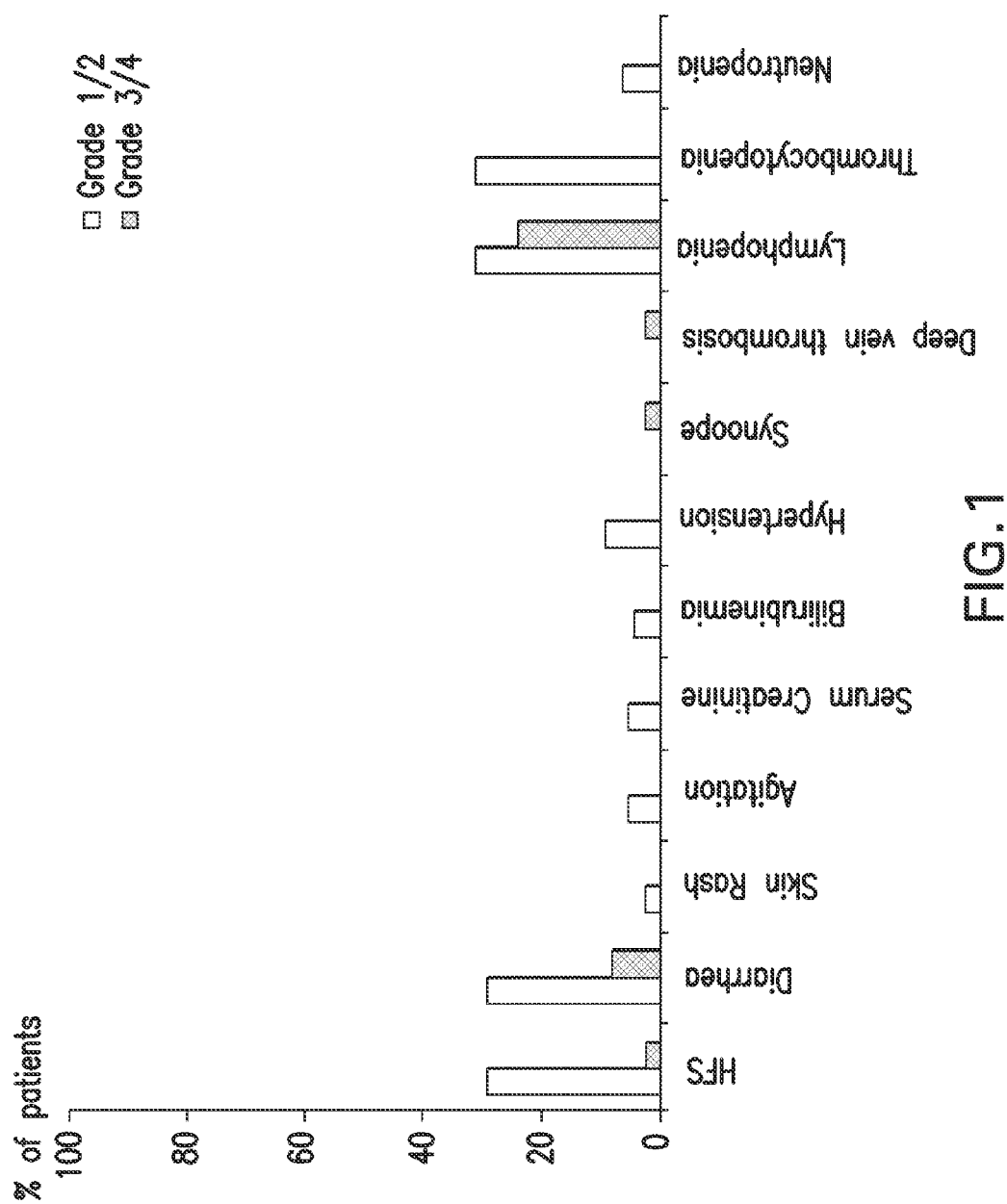
FIG. 1: Common adverse events attributable to XCEL (n=65) (study 1).

It has been recently demonstrated that the combination of chemotherapeutic agents and COX-2 inhibitors, such as celecoxib (XCEL therapy) is highly effective in treating metastatic colorectal cancer. In fact, recent studies have shown that as many as 29% of treated patients may achieve CR (U.S. Pat. No. 8,044,033). However, even in view of such success, there remains no method to predict which patients exhibit CR following such therapy. Specifically, there was previously no method to determine if a therapy such as XCEL was effective to provide a complete response to achieve molecular remission (i.e., by effectively killing cancer stem cells that may exist in the treated subject) versus those that were merely in clinical remission, but still comprised cancer stem cells. This is a significant impediment to therapy because patients that may require further anticancer therapy cannot be identified until the cancer has returned. Conversely, patients that have achieved molecular remission may continue to undergo unneeded therapies.

The studies detailed herein demonstrate that increased expression of CD133 in a subject that has undergone anticancer therapy (XCEL) can be used to determine whether the subject has had a complete response to the therapy. In particular, elevated expression of CD133 RNA in blood samples was found to be indicative of the presence of cancer stem cells. Thus, by assessing CD133 expression in patients undergoing, or who have undergone, an anticancer therapy patients can be identified that have remaining cancer stem cells versus those that have had a complete response. Specifically, it has been found that patients having a complete response to therapy have a serum CD133 RNA level less than about 0.56 (when normalized to GAPDH mRNA levels). Likewise, as compared to healthy cancer-free control subjects, complete responders exhibit serum CD133 RNA levels significantly lower than that of the healthy controls. Thus, assessment CD133 RNA levels in accordance with the embodiments, allows for early further therapeutic intervention in the case of patient found to still comprise cancer stem cells. Likewise, anticancer therapy (and the significant side effects that may accompany the therapy) can be discontinued in subjects that demonstrate a complete response to therapy.

II. Detecting Gene Expression

In certain embodiments, methods provided herein concern detecting determining a gene expression in a subject. In some aspects an expression level for CEA, CD133, CK19 and/or CK20 is determined. For example, in some embodiments, determining CD133 comprises quantifying CD133 RNA or protein expression. In some aspects, quantifying CD133 expression comprises determining CD133 expression relative to a reference gene. Methods discussed herein for determining a CD133 expression level are likewise applicable to determining the expression level of other biomarker genes such as CEA, CK19 and/or CK20.

In the clinical diagnosis and/or monitoring of subjects, the detection of increased expression of CD133, in comparison to the levels in a corresponding biological sample (i.e., a reference level) from a subject he does not have cancer or has had a complete response to an anti cancer therapy is indicative a subject that comprises cancer stem cells (or a subject that is need of a further anti-cancer therapy).

It is known to those of skill in the art that any clinical diagnosis is not necessarily be made on the basis of a single method in isolation. Accordingly, methods of the embodiments can comprise determining or obtaining the expression level or presence of two, three or more biomarkers and/or on one or more clinical symptoms in additional a CD133 expression level to diagnose a subject.

A. Nucleic Acid Detection

In some embodiments, assessing expression of CD133, can involve quantifying mRNA expression. For example, reverse transcription (RT) of RNA to cDNA followed by relative quantitative PCR™ (RT-PCR™) can be used to determine the relative concentrations of specific mRNA (e.g., a CD133 coding RNA, such as those provided by NCBI accession nos. NM_001145847.1, NM_001145848.1, NM_001145849.1, NM_001145850.1, NM_001145851.1, NM_001145852.1, or NM_006017.2, each of is incorporated herein by reference). By determining that the concentration of a specific mRNA varies relative to a reference RNA (e.g., an RNA encoding control gene such as GAPDH), it is shown that the gene encoding the specific mRNA species is differentially expressed. In certain aspects, mRNA expression can be quantified relative to the expression of such a reference mRNA. For instance, methods for quantifying CD133 mRNA expression relative to GAPDH have been previously described in Iinuma et al., 2011, the entirety of which is incorporated herein by reference.

In some embodiments, the amplification products described above may be subjected to sequence analysis to identify specific kinds of variations using standard sequence analysis techniques. Within certain methods, exhaustive analysis of genes is carried out by sequence analysis using primer sets designed for optimal sequencing. The present embodiments provide methods by which any or all of these types of analyses may be used. Using the known sequences CD133 and/or reference genes, oligonucleotide primers may be designed to permit the amplification of sequences throughout a given gene (or protein coding sequence) that may then be analyzed by direct sequencing. Likewise, DNA sequencing may be used to detect and/or quantify expression of CD133 or other marker or reference genes. Methods for such sequence include, but are not limited to, reversible terminator methods (e.g., used by Illumina® and Helicos® Biosciences), pyrosequencing (e.g., 454 sequencing from Roche) and sequencing by ligation (e.g., Life Technologies™ SOLiD™ sequencing)

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

Northern blotting techniques for detecting RNA expression are also well known to those of skill in the art. Northern blotting involves the use of RNA as a target. Briefly, a probe is used to target an RNA species that has been immobilized on a suitable matrix, often a filter of nitrocellulose. The different species should be spatially separated to facilitate analysis. This often is accomplished by gel electrophoresis of nucleic acid species followed by "blotting" on to the filter. Subsequently, the blotted target is incubated with a probe (such as a labeled probe) under conditions that promote denaturation and rehybridization. Because the probe is designed to base pair with the target, the probe will binding a portion of the target sequence under renaturing conditions. Unbound probe is then removed, and detection is accomplished.

In some embodiments, nucleic acids are quantified following gel separation and staining with ethidium bromide and visualization under UV light. In some embodiments, if the nucleic acid results from a synthesis or amplification using integral radio- or fluorometrically-labeled nucleotides, the products can then be exposed to x-ray film or visualized under the appropriate stimulating spectra, following separation.

In some embodiments, visualization is achieved indirectly. Following separation of nucleic acids, a labeled nucleic acid is brought into contact with the target sequence. The probe is conjugated to a chromophore or a radiolabel. In another embodiment, the probe is conjugated to a binding partner, such as an antibody or biotin, and the other member of the binding pair carries a detectable moiety. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present embodiments.

B. Detection of Protein

In some aspects, methods of the embodiments concern detection of the expression of CD133 protein. For example, immunodetection methods for binding, purifying, removing, quantifying and/or otherwise generally detecting protein components such as CD133 can be employed. Antibodies prepared in accordance with the present embodiments may be employed to detect CD133. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In general, the immunobinding methods include obtaining a sample suspected of containing a CD133 protein, polypeptide and/or peptide, and contacting the sample with a first anti-CD133 antibody in accordance with the present embodiments, under conditions effective to allow the formation of immunocomplexes. The antibody will preferably be linked to a solid support, such as in the form of a column matrix, and the sample suspected of containing biomarker protein antigenic component will be applied to the immobilized antibody. The unwanted components will be washed from the column, leaving the antigen immunocomplexed to the immobilized antibody, biomarker protein antigen is then collected by removing the protein and/or peptide from the column.

The immunobinding methods also include methods for detecting and quantifying the amount of a CD133 in a sample. Here, one would obtain a sample and contact the sample with an antibody and then detect and quantify the amount of immune complexes formed under the specific conditions.

In terms of antigen detection, the biological sample analyzed may be any sample that is suspected of containing a cell expressing CD133, such as a serum or whole blood sample, a tissue extract or another biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any CD133 protein antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

In some embodiments, a CD133 antibody (e.g., an anti-CD133 antibody) employed in the detection may itself be linked to a detectable label, wherein one would then simply detect this label, thereby allowing the amount of the primary immune complexes in the composition to be determined. In some embodiments, the first antibody that becomes bound within the primary immune complexes may be detected by means of a second binding ligand that has binding affinity for the antibody. In certain embodiments, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR methodology. The PCR™ method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR™ reaction with suitable primers with appropriate controls. At least in theory, the enormous amplification capability and specificity of PCR™ can be utilized to detect a single antigen molecule.

The immunodetection methods of the present embodiments have evident utility in the diagnosis and prognosis of conditions such as various forms of inflammatory disease, such as KD. Here, a biological and/or clinical sample suspected of containing a CD133 biomarker protein, polypeptide, peptide and/or mutant is used. However, these embodiments also have applications to non-clinical samples, such as in the titering of antigen or antibody samples, for example in the identification of cellular mediators of inflammation.

III. Anti-Cancer Therapies

As detailed supra certain aspects of the embodiments involve the use of anti-cancer therapies. For example, in some aspects, a subject is selected for administration of an additional anti-cancer therapy following treatment with a regimine with a fluorocytidine derivative and a COX-2 enzyme inhibitor. In some cases, such an additional anticancer therapy may be further treatment with a fluorocytidine derivative (e.g., capecitabine) and a COX-2 enzyme inhibitor (e.g., celecoxib). In still further aspects, the additional therapy can be treatment with a chemotherapy, a radiotherapy, an immunotherapy, a gene therapy, a surgical therapy or a combination thereof.

A. Chemotherapy

In certain embodiments, a subject may be treated with an additional chemo therapeutic agent. Examples of chemotherapeutic agents include without limitation alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above.

B. Radiotherapy

In certain preferred embodiments of the invention celecoxib and capecitabin may be used to sensitize cell to radiation therapy. Radio therapy may include, for example, g-rays, X-rays, and/or the directed delivery of radioisotopes to tumor cells. In certain instances microwaves and/or UV-irradiation may also used according to methods of the invention. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radio therapeutic agent are delivered to a target cell or are placed in direct juxtaposition with the target cell. To achieve cell killing or stasis, both agents are delivered to a cell in a combined amount effective to kill the cell or prevent it from dividing.

C. Anti-hormonal Agents

In certain aspects an additional anticancer therapy is an anti-hormonal therapy that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

D. Immunotherapy Agents

In some an additional anticancer therapy is an immunotherapy. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In some embodiments, an immunotherapy can comprise administering one or more tumor antigens to a patient (e.g., a cancer vaccine) or exposing a patient's immune cells to such a cancer antigen (e.g., an autologous cellular immunotherapy). Antigens that can be used in such therapeutic approaches include, but are not limited to, prostatic acid phosphotase (PAP), MUC1, HER2/neu, 5T4 (such as 5T4 expressed from a vaccinia virus vector) and whole killed cancer cells.

Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

E. Gene Therapy

In some embodiments, an additional anticancer therapy is a gene therapy (e.g., a therapeutic polynucleotide composition). Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these method are well known in the art (see, e.g. Sambrook et al., 1989; Ausubel et al., 1998; Ausubel, 1996).

Delivery of a vector encoding one of the following gene products will have a combined anti-hyperproliferative effect on target tissues.

E. Surgical Therapy

In some aspects, an additional anticancer therapy is a surgical therapy (e.g., before after or during surgical resection of a tumor). Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Additional Therapeutic Agents

In some embodiments, additional anticancer therapies comprise administration of a further agent, such as an anti-inflammatory agent. An anti-inflammatory agent is defined herein to refer to an agent that is known or suspected to be of benefit in the treatment or prevention of inflammation in a subject. Corticosteroids are a major class of anti-inflammatory agent. The corticosteroids may be short, medium, or long acting, and may be delivered in a variety of methods. A non-limiting list of corticosteroids contemplated in the present invention include the oral corticosteroids such as: cortisone, hydrocortisone, prednisone, and dexamethasone.

Another major class of anti-inflammatory agents are non-steroidal anti-inflammatory agents. Non-steroidal anti-inflammatory agents include a class of drugs used in the treatment of inflammation and pain. The exact mode of action of this class of drugs is unknown. Examples of members of this class of agents include, but are not limited to, ibuprofen, ketoprofen, flurbiprofen, nabumetone, piroxicam, naproxen, diclofenac, indomethacin, sulindac, tolmetin, etodolac, flufenamic acid, diflunisal, oxaprozin, rofecoxib, and celecoxib. One of ordinary skill in the art would be familiar with these agents. Included in this category are salicylates and derivates of salicylates, such as acetyl salicylic acid, sodium salicylate, choline salicylate, choline magnesium salicylate and diflunisal.

Other anti-inflammatory agents include anti-rheumatic agents, such as gold salts (e.g., gold sodium thiomalate, aurothioglucose, and auranofin), anti-rheumatic agents (e.g., chloroquine, hydroxychloroquine, and penicillamine), anti-histamines (e.g., diphenhydramine, chlorpheniramine, clemastine, hydroxyzine, and triprolidine), and immunosuppressive agents (e.g., methotrexate, mechlorethamine, cyclophosphamide, chlorambucil, cyclosporine, and azathioprine). Other immunosuppressive agent contemplated by the present invention is tacrolimus and everolimus. Tacrolimus suppresses interleukin-2 production associated with T-cell activation, inhibits differentiation and proliferation of cytotoxic T cells. Today, it is recognized worldwide as the cornerstone of immunosuppressant therapy. One of ordinary skill in the art would be familiar with these agents, and other members of this class of agents, as well as the mechanism of actions of these agents and indications for use of these agents.

It is contemplated that other agents may be used as additional anticancer therapies or in combination with the present embodiments. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

IV. Therapeutic Administration

In some embodiments, an effective amount of an anticancer agent or a combination there of (e.g., celecoxib and capecitabin) are administered to a patient. The term "effective amount" as used herein is defined as the amount of celecoxib and/or capecitabin of the present invention that is necessary to result in a physiological change in the patient to which it is administered either when administered alone or in combination with another cytotoxic therapy. The term "therapeutically effective amount" as used herein is defined as the amount of celecoxib and capecitabin that eliminate, decrease, delay, or minimize adverse effects of a disease (e.g., cancer or HFS). A skilled artisan readily recognizes that in many cases methods of the invention may not provide a cure but may only provide partial benefit, such as alleviation or improvement of at least one symptom. In some embodiments, a physiological change having some benefit is also considered therapeutically beneficial. It will additionally be clear that a therapeutically effective amount may be dependent upon the inclusion of additional therapeutic regimens administered concurrently or sequentially. Thus, it will be understood that in certain embodiments a physical change may constitute an enhanced effectiveness of a second therapeutic treatment.

For example, celecoxib and capecitabin may be administered to a subject per se or in the form of a pharmaceutical composition for the treatment of cancer. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

In some aspects methods of the invention concern systemic formulations include those designed for administration by injection, e.g. subcutaneous, intravenous, intramuscular, intrathecal or intraperitoneal injection, as well as those designed for transdermal, transmucosal, inhalation, oral or pulmonary administration. In the most preferred embodiments celecoxib and capecitabin are delivered by oral administration.

For injection, the proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

A. Effective Dosages

Anticancer therapies of the embodiments (e.g., celecoxib and capecitabin) will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

B. Toxicity

Preferably, a therapeutically effective dose of anti cancer therapy, such as a combination celecoxib/capecitabin therapy, will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

C. Pharmaceutical Preparations

Pharmaceutical compositions of the present invention may comprise an effective amount of an anticancer agent or a combination thereof (e.g., celecoxib and capecitabin) dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical compositions will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The compositions of the invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods for Study 1

Patients

The institutional review board of The University of Texas M. D. Anderson Cancer Center approved this retrospective expanded cohort study. Between October 2000 and December 2003, seventy-four patients with metastatic colorectal cancer received capecitabine with concurrent celecoxib (n=66), or rofecoxib (n=2), ibuprofen (n=2), sulindac (n=2) and high dose aspirin (n=2). This study analyzed sixty-six patients who received capecitabine and celecoxib (XCEL).

Treatment

Patients who did not receive concurrent radiation therapy received capecitabine orally at a dose of 1000 mg/m2/d twice daily (b.i.d) for 14 days every 21 days, except for four patients who started at 1250 mg/m2/d b.i.d and six elderly patients who started at 900 mg/m2/d b.i.d. All 34 patients who received radiation therapy received capecitabine at 1000 mg/m2/d b.i.d. Monday through Friday during radiation and continued capecitabine at 1000 mg/m2/d b.i.d. for 14 days every 21 days. The radiation was delivered to the target area using 18 MV photons with 3-D conformal planning technique. The dose of radiation was either 35-40 Gy (n=18) or >45 Gy (n=15) with dose radiation missing in one patient. All 66 patients received oral celecoxib continuously 200 mg b.i.d with one of the objectives to mitigate capecitabine induced HFS; while all patients had pain related to tumor (n=37) or musculoskeletal system (n=29). Fifteen patients had required additional opioids. No patients received pyridoxine during this study Responding patients—those who had declining carcinoembryonic antigen (CEA) levels, improved pain control, or stable or decreasing tumor size—continued XCEL until they experienced complete remission, disease progression, or intolerable side effects. All patients experienced pain relief from radiation and/or celecoxib, but formal pain scores were not performed in all patients. Celecoxib was continued with capecitabine to prevent HFS and to improve survival. Six patients had resection of their tumors with curative intent after tumors became respectable after response to XCEL alone or with radiation and four patients had XCEL postoperatively; Two patients had radiofrequency ablations and one patient had palliative resection of colon primary.

Evaluation and Definitions

All patients were subjected to routine clinical examinations, laboratory analyses, and computed tomography. Patients were seen weekly during radiotherapy if treated on site or every 6-9 weeks with physical examinations, laboratory tests, and computed tomography. Treatment-related toxicity was graded using the National Institutes of Health's Common Toxicities Criteria (CTC) version 2.0. Tumor responses were evaluated using RECIST criteria. Complete response was defined as complete radiographic disappearance of measurable or evaluable disease or stable, minimal radiographic findings; partial response was defined as reduction of the longest dimension of measurable disease by at least 50%; stable disease was defined as reduction of the longest dimension by less than 25%; These responses or stable must be confirmed at least by 3 months interval evaluation; Progressive disease was defined as growth of the tumor by more than 25% in the longest dimension or development of new lesions. Overall response rate was defined as the sum of the complete and partial response rates and the tumor control rate was defined as the sum of overall response rates with stable disease rates. The date of death was ascertained through the cancer registry or through a search of patients' social security numbers in the Social Security Death Index (ssdi.genealogy-.rootsweb.com). The cutoff point for collection of data was April 2004.

Statistical Analysis

Continuous variables were summarized using the mean (±standard deviation) or the median (range). Comparisons of these variables by patient subgroup (radiation, surgery, high or low lactate dehydrogenase (LDH), and high or low CEA were made using the Wilcoxon rank-sum test. Categorical variables were summarized in frequency tables. Comparisons of important subgroups for these variables were made using the chi-square test or Fisher's exact test, as appropriate. Progression-free survival was defined as the time from the start of XCEL therapy to disease progression or death from any cause. Overall survival was defined as the time from the start of XCEL therapy to death from any cause. Patients were censored at the date of last follow-up if they had not progressed or died. Progression-free and overall survival distributions were summarized using the method of Kaplan and Meier. Differences in progression-free and overall survival by subgroup were analyzed using the log-rank test. Multivariate models of predictors of progression-free survival and overall survival were evaluated using the proportional hazards (Cox) regression model. P<0.05 was considered statistically significant.

Example 2

The Effects of Combination Therapy (Study 1)

The patients' baseline clinical and treatment characteristics are summarized in Table 1. The median age of the 24 patients who received first-line XCEL was 73 years (range, 45-86 years), and 7 patients were 78 years or older. Of the 42 patients who received XCEL as second-line therapy, 9 were still responding to the first-line treatment or sensitive to irinotecan-based treatment, the remaining 33 patients' disease had progressed during the first-line treatment. Twenty-four (71%) of the 34 patients who received radiation had prior first-line chemotherapy.

TABLE 1

Baseline Patient, Disease, and Treatment Characteristics (n = 21)

| Category | No. of patients (%) |
|---|---|
| Median age (range) | 64 (30-82 years) |
| <64 years | 11 (52) |
| ≥64 years | 10 (48) |
| Sex | |
| Male | 13 (62) |
| Female | 8 (38) |
| Race | |
| White | 21 (100) |
| Eastern Cooperative Group (ECOG) performance status | |
| 0 | 12 (68) |
| 1 | 8 (38) |
| 2 | 1 (5) |
| Primary colon cancer | 14 (67) |
| Primary rectal cancer | 7 (33) |
| Initial AJCC Stages | |
| II | 4 (19) |
| III | 8 (38) |
| IV | 9 (43) |
| Median disease free interval before metastasis (range) | 6 month (0-72 months) |
| Prior adjuvant 5FU treatment | 8 (45) |
| Median time of last 5-FU treatment to stage IV | 6 months (0-54) |
| Solitary/clustered nodal metastasis | 12 (68) |
| Median Size (range) | 3 cm (2-8.5 cm) |
| Para-aortic and retroperitoneal node[††] | 7 (33) |
| Liver[†] | 2 (9) |
| Pelvis[†] | 2 (9) |
| Lung | 1 (5) |
| Abdominal wall | 1 (5) |
| None-solitary metastasis | 9 (42) |
| Median size (range) | 3 cm (0.8-15 cm) |
| Median number of metastasis (range) | 4 (2-9) |
| Liver | 4 (19) |
| Liver + lung | 2 (9) |
| Carcinomatosis | 2 (9) |
| Lung | 1 (5) |
| LDH > upper limit of normal | 2 (9) |
| CEA > 3.0 ng/ml (range 3-28) | 8 (38) |
| No radiation | 8 (38) |
| Radiation ≥ 45 Gy | 8 (38) |
| Radiation < 45 Gy | 5 (24) |
| Firstline XCEL | 8 (38) |
| First-line Irinotecan regimens^ | 13 (62) |
| Surgery | 6 (17) |
| Pelvis[†] | 2 (11) |
| Liver[†] | 3 (6) |
| Lung | 2 (6) |
| Third-line or fourth line treatment | 3 (17) |

[††]Three patients had four or more clustered nodal metastases.
[†]One patient with synchronous rectal tumor and a solitary liver metastasis
^Include 9 patients who responded to first-line Irinotecan with 5-FU, leucovorin or capecitabine.

Toxicities

The median duration of XCEL treatment was 7.2 months (range, 1.5-38 months). Adverse events were available for all but one patient (n=65) summarized in FIG. 1. Most common reason for discontinuing XCEL was progressive disease (n=46). Most common toxicity was lymphopenia of all grades (56%) with 24% being grade ¾ lymphopenia. Incidence of grade 1, 2 and 3 HFS was 14%, 15% and 2% respectively and the median times to HFS onset and peak were 3.8 months (n=17) and 6.0 months (n=12), respectively. Ninety percent of the grade ⅔ HFS occurred after 6 months. Mild serum creatinine elevations (1.6-2.0 mg/dL) occurred in 3 patients after 14 to 32 months of XCEL reversible upon discontinuation of celecoxib. Celecoxib was also discontinued due to grade 2 skin rash (n=1) and grade 2 agitations (n=3). A 56-year-old man experienced two episodes of syncope on cycle 3 and 4 of XCEL presumably because of postural hypotension. No gastrointestinal bleeding, other cardiovascular events, or deaths were noted.

Response Rate

Figure 2:
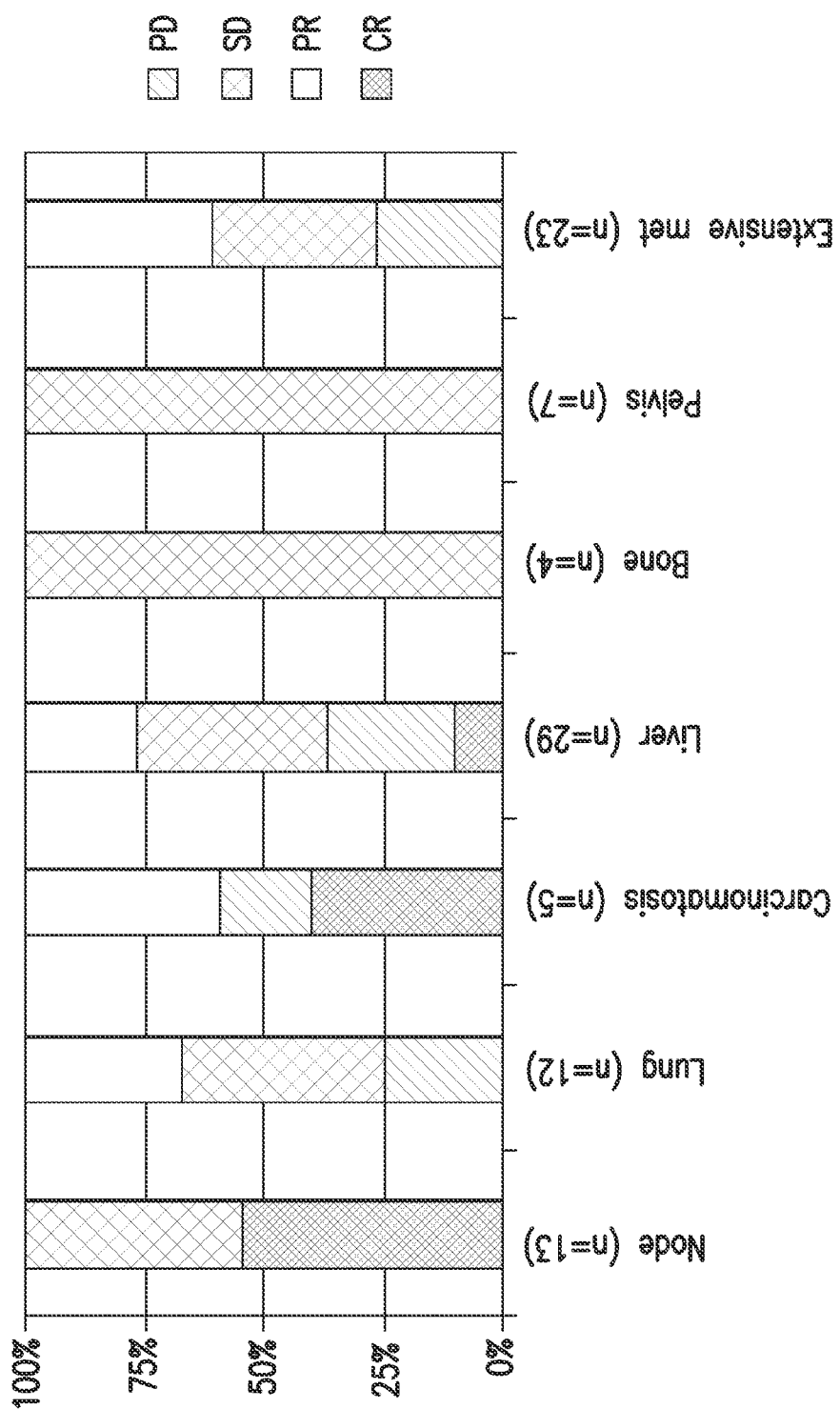
FIG. 2: Response rate by disease sites (study 1).

Of the 66 patients, 13 (20%) achieved a complete response (CR), 12 (18%) achieved a partial response (PR), and 25 (38%) had stable disease (SD), yielding an overall response rate of 38% (95% CI, 26-51%) and a tumor control rate of 76% (95% CI, 60-83%). Of the 24 patients with first-line XCEL, 4 (17%) achieved CR with an overall response rate of 34% (95% CI, 16-55%) and a tumor control rate of 84% (95% CI, 63-95%). Of the 28 patients who had progressed on 5FU and irinotecan and received second-line XCEL, 2 (7%) achieved CR, with an overall response rate of 25% (95% CI, 11-45%) and a tumor control rate of 68% (95% CI, 45-80%). The second line overall response rate was 40.5% (95% CI, 27-53%) when all 9 first-line irinotecan responders were included. Complete responses occurred predominantly in patients who received first-line XCEL or after first-line response to irinotecan-based therapy where 7 of 9 patients achieved complete response plus one near complete response (Tables 2 and Table 3). The most common site of complete response was nodal metastasis (51%) followed by peritoneum (40%). No CR was observed for patients with extensive multi-visceral metastasis, but partial responses were seen in all sites except for bone and pelvic metastasis (FIG. 2). Of six patients who had surgery with curative intent, one had pathological CR, 4 had PR and 1 SD from XCEL alone (n=2) or with radiation (n=4).

TABLE 2

Response to XCEL With or Without Radiation

| | No. of patients (%) | |
|---|---|---|
| Tumor response | Radiation (n = 34) | No radiation (n = 32) |
| Complete response | 9 (26) | 4 (13) |
| Partial response | 6 (18) | 6 (19) |
| Overall response | 15 (44) | 10 (31) |
| Stable disease (>4 months) | 12 (35) | 13 (41) |
| Tumor control | 27 (79) | 23 (72) |

TABLE 2.1

Tumor characteristics, Prior therapies, XCEL duration and Subsequent Therapy (N = 21).

| No. | Sex | Tumor site(s) | Size (cm) | No | Initial Rx | RT (Gy) | 1st line RR, Surgery (Margin in mm) | RR XCEL | XCEL Duration | CR duration Months | OS from 1st Rx | OS from XCEL | Subsequent Treatments |
|---|---|---|---|---|---|---|---|---|---|---|---|---|---|
| 1 | 30 M | Liver and rectum | 8.5 | 1 | IFL | 45 | PR, LAR, R Hepatectomy (20 mm) | pCR | 3 mo | 20.5+ | 39+ | 34+ | |
| 2 | 64 F | Para-aortic nodes | 2.6 | 1† | IRI | 50.4 | PR | CR | 22+ | 19+ | 27+ | 22+ | |
| 3 | 75 M | Liver and lung | 0.8 | 5 | XELIRI | — | PR | CR | 12 | 21+ | 28+ | 24+ | |
| 4 | 53 M | Liver | 1.5 | 9 | IFL; XELIRI | — | PR or Near CR | CR | 24 | 28+ | 39+ | 30+ | |
| 5 | 61 F | Mesenteric node | 3 cm | 1 | XELIRI | 45 | PR or Near CR | CR | 5.5 | 27.5+ | 39+ | 30.5+ | |
| 6 | 54 M | Gastrohepatic nodes | 2.2 | 6 | XELIRI | 50.4 | PR | CR | 29 | 14 | 36+ | 27+ | Repeat XCEL radiation, IRI |
| 7 | 67 M | Carcinomatosis | NA | - | XELIRI | — | NA | CR | 3.5 | 13+ | 24+ | 16+ | |
| 8 | 60 M | Aortocaval node | 3.5 | 1 | IFL | 35 | PD | CR | 39+ | 32+ | 59+ | 39+ | Capecitabine alone |
| 9 | 36 F | Para-aortic node | 2.5 | 1† | IFL | 50.4 | PD | CR | 34+ | 36+ | 48+ | 43+ | |
| 10 | 52 F | Liver | 3 | 4 | XELIRI | — | PR | CR | 24+ | 14+ | 30+ | 24+ | |
| 11 | 64 M | Para-aortic node | 2 | 1† | IFL | 35 | PD | SD | 14 | 0 | 51.5+ | 42+ | IFL + Bev, FOLFOX |
| 12 | 49 F | Liver, lung | 3 | 5 | XELIRI | — | PR | PD | 2.5 | 0 | 63+ | 22+ | FOLFOX |
| 13 | 70 M | Inguinal node | 3 | 1 | XCEL | 45 | — | CR | 1.8 | 6 | 36+ | 29+ | None; Alzheimer disease |
| 14 | 64 F | Peritoneal metastasis | 5 | 1 | XCEL | 50.4 | — | CR | 12 | 17 | 26 | 26 | None; patient's choice |
| 15 | 76 M | Retroperitoneal node | 2.6 | 1 | XCEL | — | — | CR | 43+ | 40+ | 46+ | 43+ | |
| 16 | 76 M | Liver | 3 | 1 | XCEL | 50.4 | — | CR | 9 | 10 | 48+ | 35+ | RFA to liver |
| 17 | 62 F | Pelvis | 8 | 1 | XCEL | 39 | SD, APR (Positive margin) | sCR | 6 | 53+ | 57+ | 56+ | |
| 18 | 45 F | Right lung | 2 | 1 | XCEL | — | SD, Wedge (8 mm) | sCR | 16 | 8 | 64 | 39 | IRI, FOLFOX, |
| 19 | 82 M | Lung | 8 | 3 | XCEL | 40 | PR, Wedge (30 mm) | sCR | 4 | 6 | 40 | 38 | XELRI, FOLFOX |
| 20 | 64 M | Liver | 15 | 3 | XCEL | 45 | SD, R Hepatectomy (<1 mm) | sCR | 7 | 8.7 | 47+ | 46+ | FOLFOX, IRI, Erbitux, XCEL |

TABLE 2.1-continued

Tumor characteristics, Prior therapies, XCEL duration and Subsequent Therapy (N = 21).

| No. | Sex | Tumor site(s) | Size (cm) | Initial No | Rx | RT (Gy) | 1st line RR, Surgery (Margin in mm) | RR XCEL | XCEL Duration | CR duration Months | OS from 1st Rx | OS from XCEL | Subsequent Treatments |
|---|---|---|---|---|---|---|---|---|---|---|---|---|---|
| 21 | 51 M | Liver | 8 | 2 | IROX | 50.4 | PD R Hepatectomy (1 mm) | sCR | 18 | 13 | 44 | 42 | XCEL, FOLFOX, IRI-Erbitux |

†At least 3-4 clusters nodal metastasis;
XX: first-line responders;
pCR = pathological complete response;
sCR = surgical complete response;
RT = Radiation therapy;
XELIRI = capecitabine + irinotecan;
IFL = 5FU, leucovorin andirinotecan,
CR = complete response.
*History of right hepatic lobectomy
**History of left pneumectomy;
Disease free survival was 8 months after wedge resection TABLE 3-continued First Line or Second Line XCEL Response With or Without Radition

| | No. of patients (%) | | | | | |
|---|---|---|---|---|---|---|
| | First-line | | Second-line[a] | | First-line responders[b] | |
| Respone Rate | Radition (n = 10) | No radition (n = 14) | Radition (n = 20) | No radition (n = 13) | Radition (n = 4) | No radition (n = 5) |
| Complete response | 3 (30) | 1 (7) | 2 (10) | 0 | 3 (75) | 4 (80) |
| Partial response | 3 (20) | 3 (21) | 5 (25) | 2 (15) | 1 (0) | 0 (0) |
| Overall response | 4 (40) | 4 (29) | 7 (35) | 2 (15) | 4 (100) | 4 (80) |
| Stable disease | 4 (40) | 8 (57) | 8 (40) | 5 (38) | 0 (0) | 0 (0) |
| Tumor control | 8 (80) | 12 (86) | 15 (75) | 7 (54) | 4 (100) | 4 (80) |

[a]also including five patients who prorgressed on first-line irinotecan and oxaliplatin (IROX).
[b]Seven of nine first-line irinotecan responder achieved completer response and one had near complete response.

Survival Analysis

Figure 3:
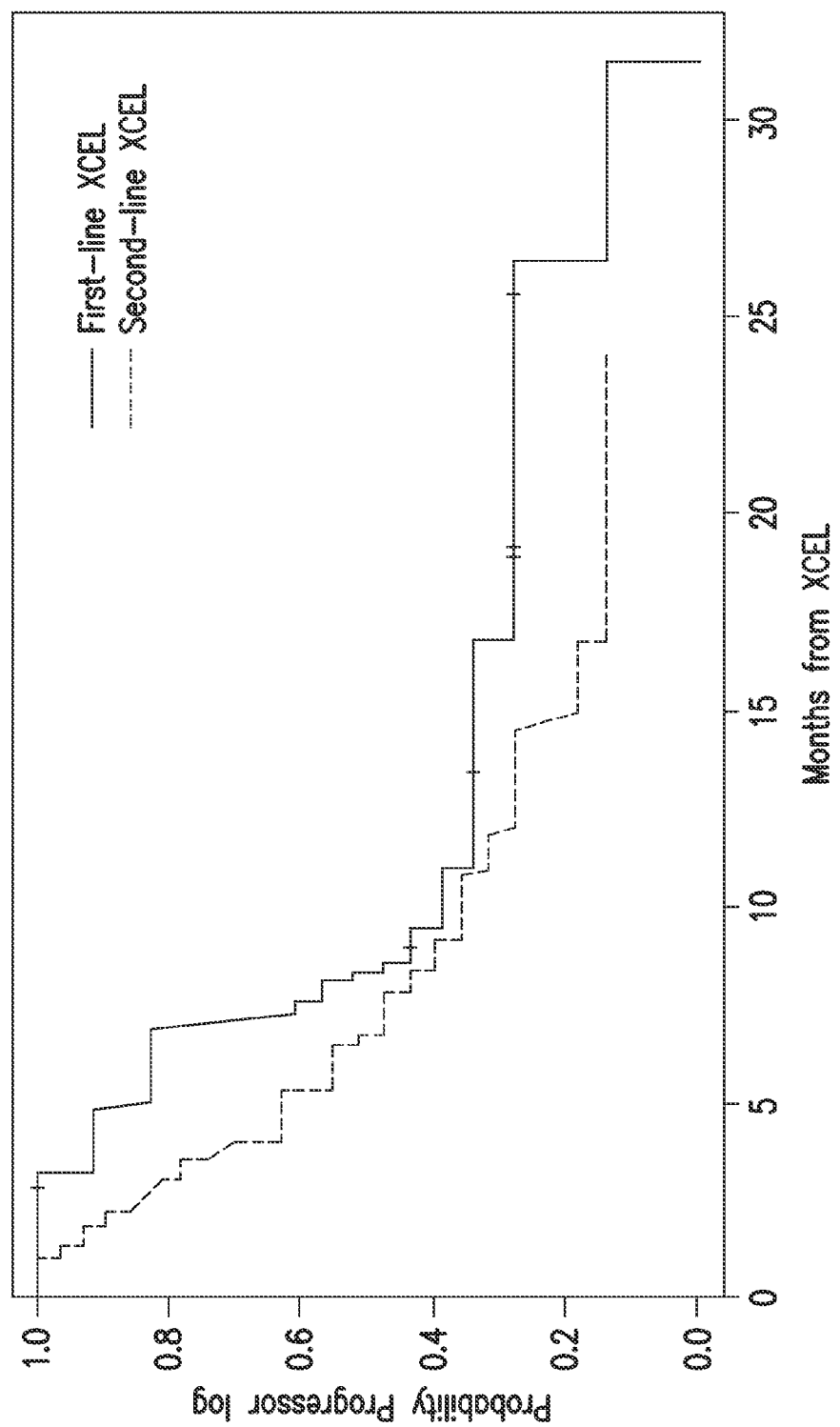
FIG. 3: Kaplan-Meier survival analysis of patients receiving XCEL as first-line or second-line therapy. Graph illustrates progression-free survival (study 1).
Figure 4:
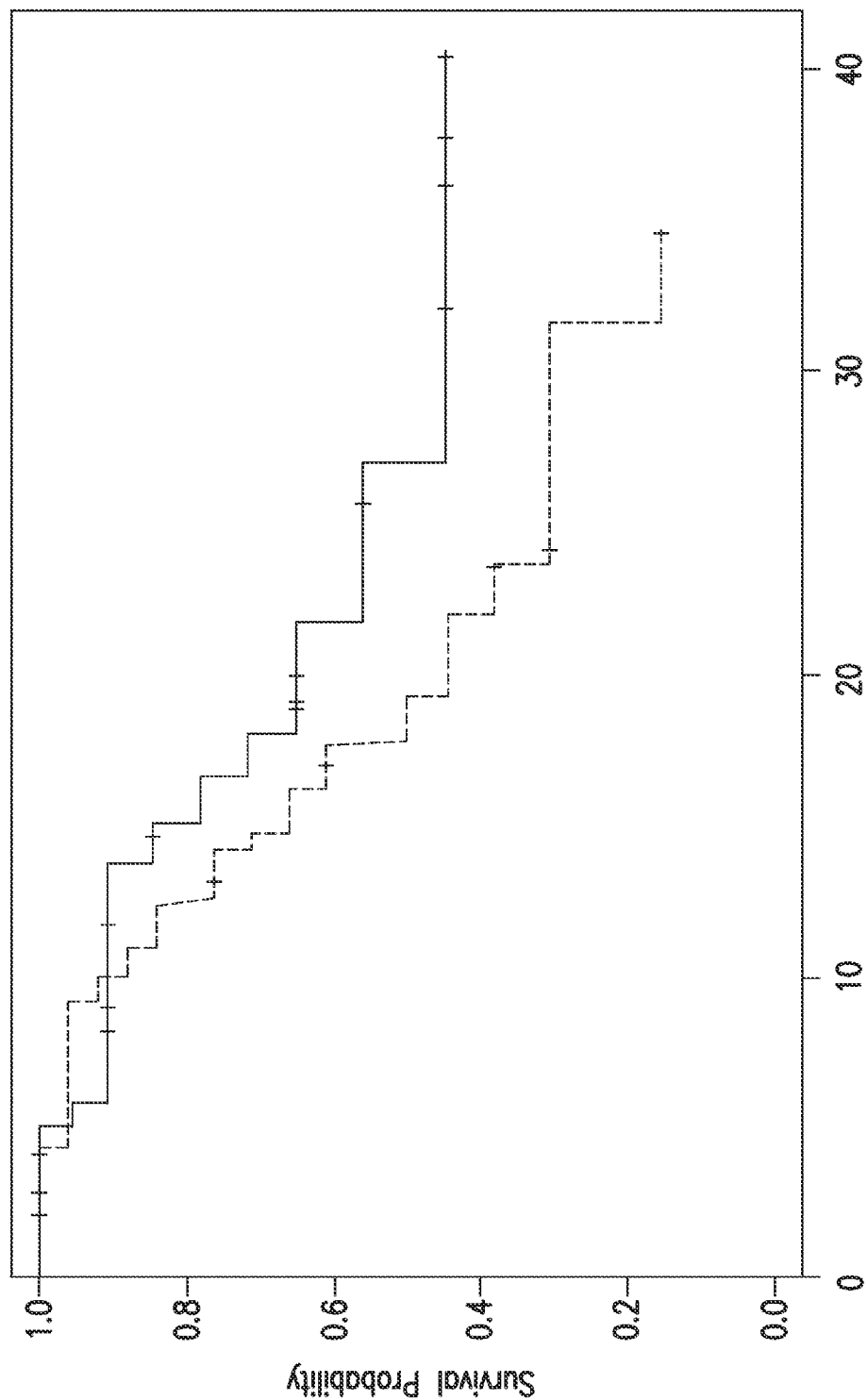
FIG. 4: Kaplan-Meier survival analysis of patients receiving XCEL as first-line or second-line therapy. Graph illustrates overall survival (study 1).

The results of the multivariate analysis of progression-free survival (PFS) and overall survival (OS) are summarized in Table 4. The median PFS was 8.3 months (95% CI, 7.1-16.8 months) for first-line XCEL versus 6.7 months (95% CI, 4.0-11.9 months) for second-line irinotecan refractory group (FIG. 3). The median overall survival was 26.9 months (95% CI 18.0 months-endpoint not reached [NR]) for first-line XCEL versus 17.8 months (95% CI, 14.7-31.5 months) for second-line irinotecan refractory (FIG. 4). The median progression free and median overall survival was 8.3 (5.4-14.5) and 19.3 months (95% CI, 16.2-31.5), respectively when 9 first-line responding patients was included. Median PFS of 21.2 months in patients who received XCEL and radiation (>45 Gy) did not result in prolongation of median OS (P=0.75), but a subset of patients whose median PFS and OS were not reached. Favorable median PFS in patients with normal levels of CEA (P=0.02) and normal levels of LDH (P<0.0001) resulted in improvement of OS for patients with normal LDH (P=0.005); Improvement of OS was also noted in patients who had surgery and radiofrequency ablation (P=0.003).

TABLE 4

Time-to-Event Analysis of Patients Receiving XCEL With or Without Radition*

| | Progression-free survial (months) | | | Overall Survival (months) | | |
|---|---|---|---|---|---|---|
| Category | E/N | Median (95% CI) | P value | E/N | Median (95% CI) | P value |
| All | 46/66 | 8.3 (7.0-11.0) | NA | 26/66 | 22.0 (17.8-31.5) | NA |
| No surgery | 39/57 | 7.8 (6.4-9.4) | | 25/57 | 19.3 (16.2-26.9) | |
| Surgery | 7/9 | 16.8 (8.3-31.4) | 0.13 | 1/9 | NR | 0.003 |
| No Radiation (RT) | 25/32 | 7.2 (4.8-9.4) | | 14/32 | 20.0 (16.6-22.8) | |
| RT <45 Gy | 14/18 | 8.0 (6.4-14.6) | 0.17 | 9/18 | 20.0 (14.7-NR) | 0.75 |
| RT ≥45 Gy | 6/15 | 21.2 (7.1-21.2) | | 3/15 | 21.8 (17.6-NR) | |
| CEA ≤3.0 ng/ml | 6/17 | 16.8 (9.4-NR) | | 3/17 | 31.5 (18.0-NR) | |

TABLE 4-continued

Time-to-Event Analysis of Patients Receiving XCEL With or Without Radition*

| | Progression-free survial (months) | | | Overall Survival (months) | | |
|---|---|---|---|---|---|---|
| Category | E/N | Median (95% CI) | P value | E/N | Median (95% CI) | P value |
| CEA >3.0 ng/ml | 35/44 | 7.1 (5.7-9.4) | 0.02 | 23/44 | 20.0 (16.2-26.9) | 0.12 |
| LDH ≤618 | 20/37 | 14.5 (9.2-26.3) | | 8/37 | 31.5 (23.6-NR) | |
| LDH >618 | 26/29 | 6.4 (4.3-7.2) | <0.0001 | 18/29 | 17.6 (14.7-20.0) | 0.005 |

E/N: events/numbers of patients;
NR: Not reached;
NA: not applicable.
*One patient treated outside the institution did not have radiation dose.

Discussion

XCEL with radiation resulted in far superior complete response rate, median progression-free survival, and median overall survival compared with historical control with capecitabine monotherapy. These findings also compared favorably to that of combination chemotherapy in first-line and second-line treatment of metastatic colorectal cancer though there are many caveats of making cross-study comparisons (Table 5). The current study findings was limited by its retrospective design and small sample size, and use of radiation that confounded the role of celecoxib in response rate interpretation but not in toxicities; nonetheless, the patients' tumor characteristics were comparable to other studies and median overall survival of 31 months, a finding compatible to that of highly selected surgical series was achieved in 37 patients (56%) who presented with normal level of LDH.29 Furthermore, only 18 patients (28%) of the patients had received all three agents 5-FU, irinotecan, and oxaliplatin, because more than 70% of the patients received XCEL from a period that oxaliplatin was not available in the U.S. The median overall survival was projected to be 14 months based on the Grothey's model that plots percentage of patients who had received 5FU, irinotecan and oxaliplatin to median survival, implicating durable antitumor activity of XCEL (Grothey et al., 2004).

arterial infusion of fluorodeoxyuridine was associated with increased response rate (including complete response) and survival for patients with liver only metastasis (Ben-Josef et al., 2005). The study and others may herald a trend of moving chemo-radiation beyond the palliative role in the treatment of selected metastatic colorectal cancer patients especially in view of nineteen (29%) complete responses. Detailed clinical and tumor characteristics of complete responses will be discussed in another report. Trimodal treatment capecitabine, celecoxib and radiation in a xenograft pancreas tumor model produced synergistic antitumor effects in both shielded and irradiated tumors, indicating the abscopal effect also observed in the current study (Blanquicett et al., 2005). In contrast, phase II studies combining high dose rofecoxib with bolus 5-FU and leucovorin or combining celecoxib with capecitabine, irinotecan found no added antitumor activity in patients with metastatic colorectal cancer (Becerra et al., 2003; El-Rayes et al., 2005).

Earlier study controlled for capecitabine dose at 1000 mg/m2/d bid indicated that XCEL was associated with lower incidence of grade ⅔ HFS (12.5% versus 34.2%) than capecitabine alone (p=0.037) and reduced grade ¾ diarrhea (Lin et al., 2002). In this expanded study with longer follow up, XCEL resulted in 17% of grade ⅔ HFS, 90% of which occurred after 6 months and median HFS onset and peak

TABLE 5

Cross-study comparison of XCEL to other first-line and second-line therapy

| Category | Capecitabine | XELIRI | IFL + B[c] | XCEL | FOLFOX = B | Capecitabine | XCEL |
|---|---|---|---|---|---|---|---|
| | First-line therpoy | | | | Second-line theropy | | |
| Number of patients | 1200 | 52 | 402 | 24 | 290 | 22 | 28 |
| Radiation | No | No | No | No | No | No | Yes |
| Refactry to | None | None | None | None | None | 5-FU | 5-FU, IRI |
| Complete response (%) | 3 | 0 | 4 | 17 | 5-FU, IRI | 0 | 7 |
| Response rate (%) | 19-25 | 50 | 45 | 33 | 9-20 | 0 | 25 |
| Stable disease (%) | 50 | 21 | NA | 50 | 45-51 | 50 | 50 |
| Median PFS (months) | 4.2 | 7.8 | 10.6 | 8.3 | 4-6 | 2.1 | 6.7 |
| Median OS (months | 12.4-13.2 | 16.8 | 20.3 | 26.9 | 9.8-12 | 12.2 | 17.6 |

NA: Not available;
B: bevacizumab;
XELIRI: capecitabine and irinotecan;
IRI: irinotecan;
FOLFOX: infusional 5-FU +/− LHOP;
PFS: progession-free survival;
OS: overall survival Radiation is historically reserved as a palliative tool for patients with metastatic colorectal cancer, but was the main stay of treatment for patients with locally advanced rectal cancer, in whom 20-30% of complete pathological response had been observed with concurrent infusional 5FU or capecitabine (Dawson et al., 2000; Janjan et al., 2000; Lin et al., 2005). Escalated dose of radiation with concurrent hepatic occurring at 3.8 months and 6 months respectively. In contrast, patients experienced HFS onset (93%) and most severe episode (67.9%) within six weeks of capecitabine at 1250 mg/m2/d and as high as 17% were grade 3 HFS. Reduced HFS manifestations in the current study could not be simply attributable only to lower dose of capecitabine at 1000 mg/m2/d, as capecitabine starting at 750-1000 mg/m2/d bid with irinotecan also produced 35% HFS (Patt et al., 2004). More importantly, half of the patients on monotherapy capecitabine would have experienced tumor progression (2-4 months) prior to HFS peak of 6 months observed in XCEL study (Van Cutsem et al., 2001; Hoff et al., 2001; Hoff et al., 2004; Lee et al., 2004). Furthermore, lack of HFS time course would also make cross-study comparison of HFS incidences difficult, as celecoxib may not only affect HFS incidence but also may delay its onset and peak (Abushullaih et al., 2002; Hoff et al., 2004; Lee et al., 2004). Nevertheless, this hypothesis is being tested in a National Cancer Institute sponsored prospective, randomized phase III study that compares celecoxib versus placebo on capecitabine-induced HFS in patients with metastatic colorectal and metastatic breast cancers stratified to radiation or no radiation.

Figure 6:
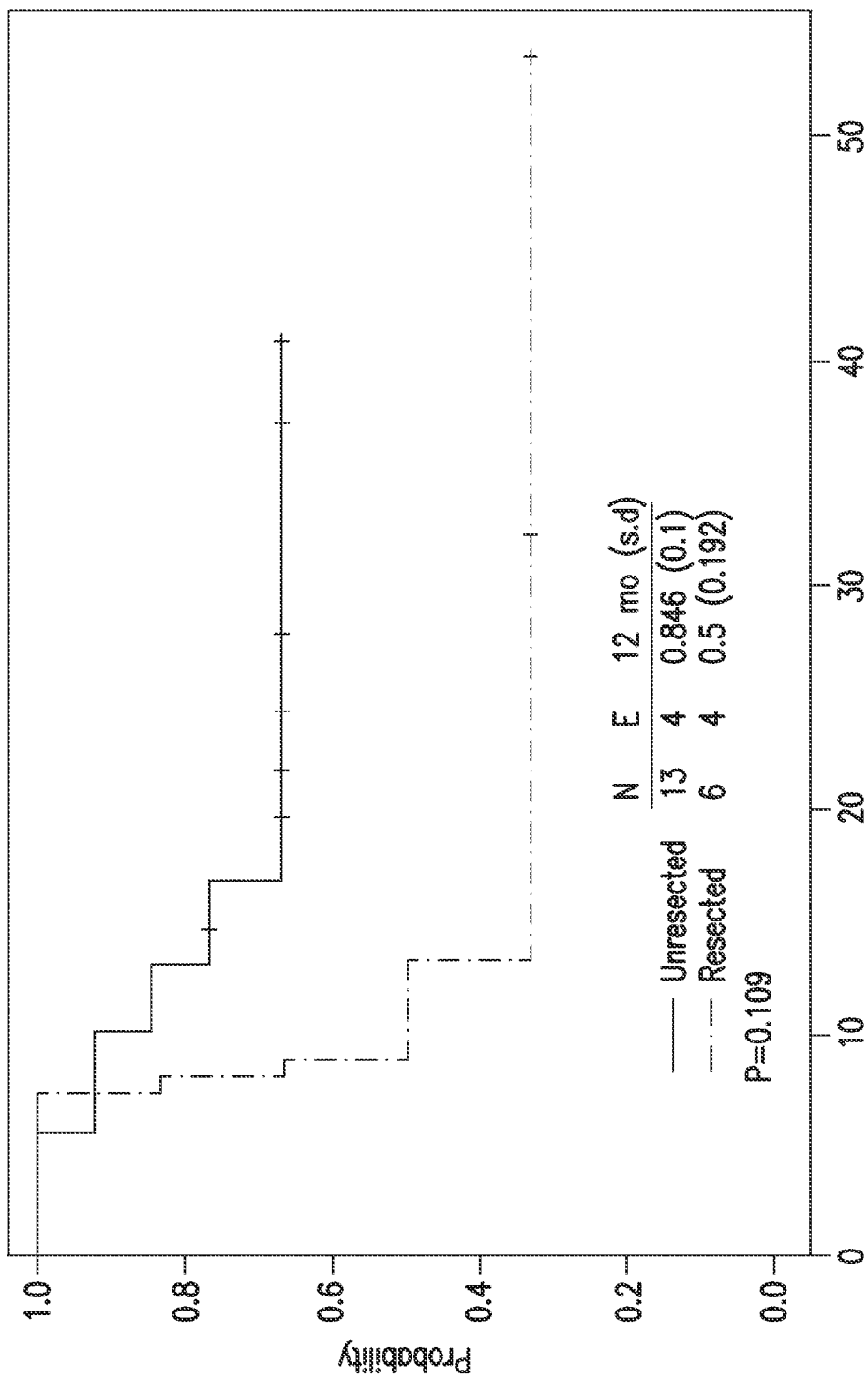
FIG. 6: Complete response duration in resected (n=6) and unresected patients (n=13) (study 2).

Improved clinical outcomes and reduced toxicities with XCEL supported our initial hypothesis that COX-2 activation, a key playmaker of inflammation may be the common mechanism mediating HFS and colorectal cancer progression (FIG. 6). HFS bears all four pathognomic signs of inflammation as well as occasional arthritis flare-up and biopsies of HFS lesions revealed acute inflammatory dermal and vascular injuries (Nagore et al., 2000; Lin et al., 2002). Interestingly, incidence of diarrhea and indirect bilirubinemia, which involves inflammation as well appeared also reduced with XCEL (Lin et al., 2002). Many none-5FU cytotoxic agents e.g. liposomal doxorubicin, cytarabine, vinorelbine, docetaxel as well as cytostatic tyrosine kinase inhibitor of vascular endothelial growth factor receptor (VEGFR) are also known to cause HFS, indicating a common pathophysiological pathway that predisposes hand-foot tissues to these offending agents (Nagore et al., 2000; Escudier et al., 2005; Demetri et al., 2005). Though not studied in the normal hand-foot tissues, COX-2 activation in the tumor in response to chemotherapy and/or radiation was well documented both in experimental models and in patients (Mercer et al., 2005; Altorki et al., 2005). Co-treatment with celecoxib with chemotherapy abrogates the chemotherapy-induced increase in prostaglandin E2 level but not in COX-2 expression in the tumor (Altorki et al., 2005). Besides increased platelet aggregation thanks to unopposed action of thromboxane A2 (Topol, 2005), selective COX-2 inhibitor down regulates VEGF, the ligand of VEGFR and upregulates endostatin and thrombospondin-1, tilting to angiogenic milieu favoring microvascular injuries (Kang et al., 2002; Ma et al., 2002). These antiangiogenic mechanisms explain rapid tumor response, improved survival, and rare reversible renal dysfunction with XCEL (Kang et al., 2002). In contrast, the pathophysiology of HFS would be pro-angiogenic (acute inflammatory) tissue injuries, thus capecitabine induced HFS was reduced with concurrent use of celecoxib. Rare but fatal gastrointestinal and cardiovascular events seen with long-term celecoxib use (Goldstein et al., 2000; Solomon et al., 2005) were fortunately not seen, because current study was small and involved relative short term XCEL that targeted tumor endothelial cells whose turnover rate (2.4—13 days) was 20-2000 times faster than that of normal tissues (47-23,000 days) (Hobson and Denekamp, 1984).

In summary, capecitabine and celecoxib integrating radiation may improve tumor response and survival while may reduce toxicities notably HFS for patient with metastatic colorectal cancer, implicating COX-2 activation as the common mediator. Further understanding of the mechanisms of in vivo COX-2 activation to chemotherapy and/or radiation in normal and tumor tissues may lead to optimal ways of disrupting the COX-2 signaling pathway and improving tumor control through enhanced antiangiogenic strategies including the use of chemo-radiation while preserving the microvascular health particularly in the vital organs.

Example 3

Materials and Methods for Study 2

Patients and Treatment

This retrospective study was approved by the institutional review board of The University of Texas M. D. Anderson Cancer Center. All sixty-six patients received concurrent capecitabine (Xeloda, Roche Nutley, N.J.) at mean daily dose 1000 mg/m$^2$/d bid for 14 days every 21 days or Monday-through Friday with radiation with daily celecoxib (CELEBREX®, Pfizer, N.Y.) at 200 mg PO b.i.d. from October 2000 to December 2003.

Evaluation and Definitions

All patients were subjected to routine clinical examinations, laboratory analyses, and computed tomography before receiving XCEL described previously. All patient data were to be independently audited and radiographic images depicting CR were reviewed and agreed upon by two independent radiologists. All 19 patients had pathological confirmation of metastatic cancer ( ). Treatment-related toxicity was graded using the National Institutes of Health's Common Terminology Criteria for Adverse Events, version 3.0. Tumor responses were evaluated using RECIST criteria with complete response defined as complete radiographic disappearance of measurable or evaluable disease and normalization of tumor marker. The death date was ascertained by searching (ssdi.genealogy.rootsweb.com) using social security numbers. The cutoff point for collection of survival was October 2005.

Statistical Analysis

Continuous variables were summarized using the mean (±standard deviation) or the median (range). Categorical variables were summarized in frequency tables. Comparisons of important subgroups for these variables were made using the chi-square test or Fisher's exact test, as appropriate. Time to complete response was defined as time to start XCEL therapy to first documented radiographic complete response. Duration of complete response was defined as time to first CR to first recurrence or death. Progression free survival was defined as the time from the start of XCEL therapy to disease progression or death from any cause. Overall survival was defined as the time from the start of XCEL therapy to death from any cause. Patients were censored at the date of last follow-up if they had not progressed or died. Progression-free and overall survival distributions were summarized using the method of Kaplan and Meier. All response rates, progression-free survival and overall survival were calculated based on the 95% confidence interval (CI). Event chart was created using symbolized events versus time descriptively.

Example 4

Effects of Combination Therapy (Study 2)

The patients' baseline demographics were summarized in Table 1. All nineteen complete responders were among 21 patients who had solitary/clustered nodal metastasis (n=7) or visceral metastasis (n=5) and/or who had responded to first-line irinotecan (n=9). Unfavorable tumor characteristics were node positive primary (84%), extrahepatic disease (80%), multifocal disease (68%), synchronous primary (33%) and greater than 5 cm tumors (24%). The favorable tumor characteristics were solitary metastasis (42%), normal levels of lactate dehydrogenase (95%) and carcinoma embryonic antigen level <200 ng/ml (95%) and prior response to first-line treatment (43%). However, all patients were unresectable (n=17) or borderline resectable (n=2) including 9 patients with solitary visceral metastasis 3 were found unresectable on surgical explorations, 3 already had prior surgeries, and 3 had significant medical co-morbidities that prohibit surgery (Janjan et al., 2000). The natural history of disease in reference to XCEL treatment and subsequent therapy is summarized by event charts in Table 2 and FIG. 5.

Complete Responses

The median time to CR was 6.5 months (range, 2.5-12.5 months) and the median duration of CR was 13 months for the resected patients, but was not reached for the unresected patients (FIG. 6). All nine patients who had elevated carcinoma embryonic antigen level experienced normalization of CEA (not shown). Of the unresected patients, the most common CR site was nodal disease (43%) followed by liver (36%) and carcinomatosis (21%). Response to XCEL prior to surgery among for the 6 surgical patients was pathological CR (n=1), partial response (n=4) and stable disease (n=1). Eight of nine first-line responders achieved CR except for one none-compliant patient, who progressed on XCEL despite excellent response to first-line XELIR1. Only one of eight patients with solitary or clustered nodal disease who did not attain CR was a 55 year-old man who was refractory to IFL, then enjoyed stable disease on XCEL plus radiation for 18 months. H is disease was stable remained on for 18 months before developing lung and bone metastasis and is currently alive at 51.5+ months since diagnosis.

PFS and OS and Relapse

Figure 5:
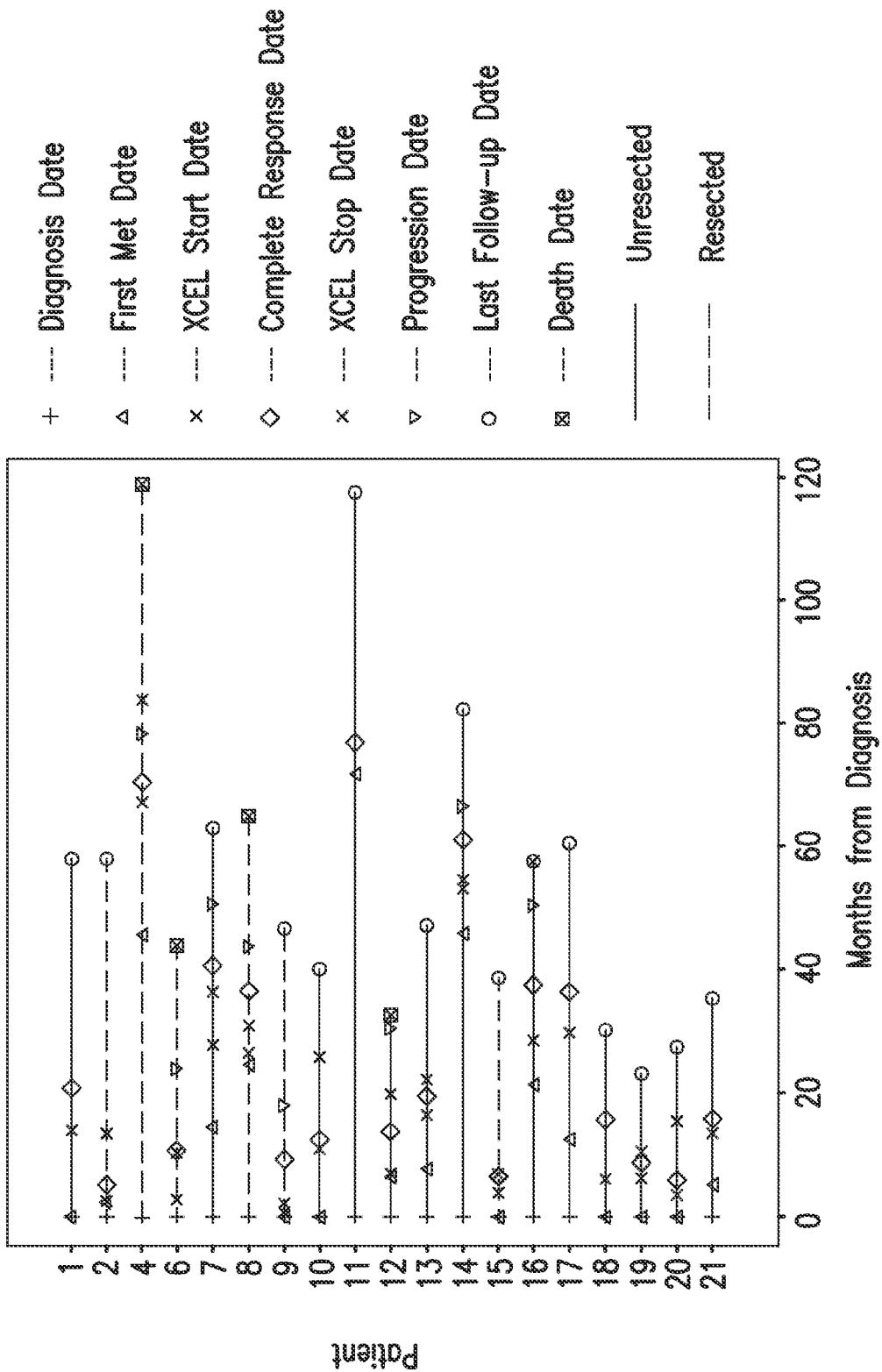
FIG. 5: Event Chart analysis (n=21) (study 2).
Figure 7:
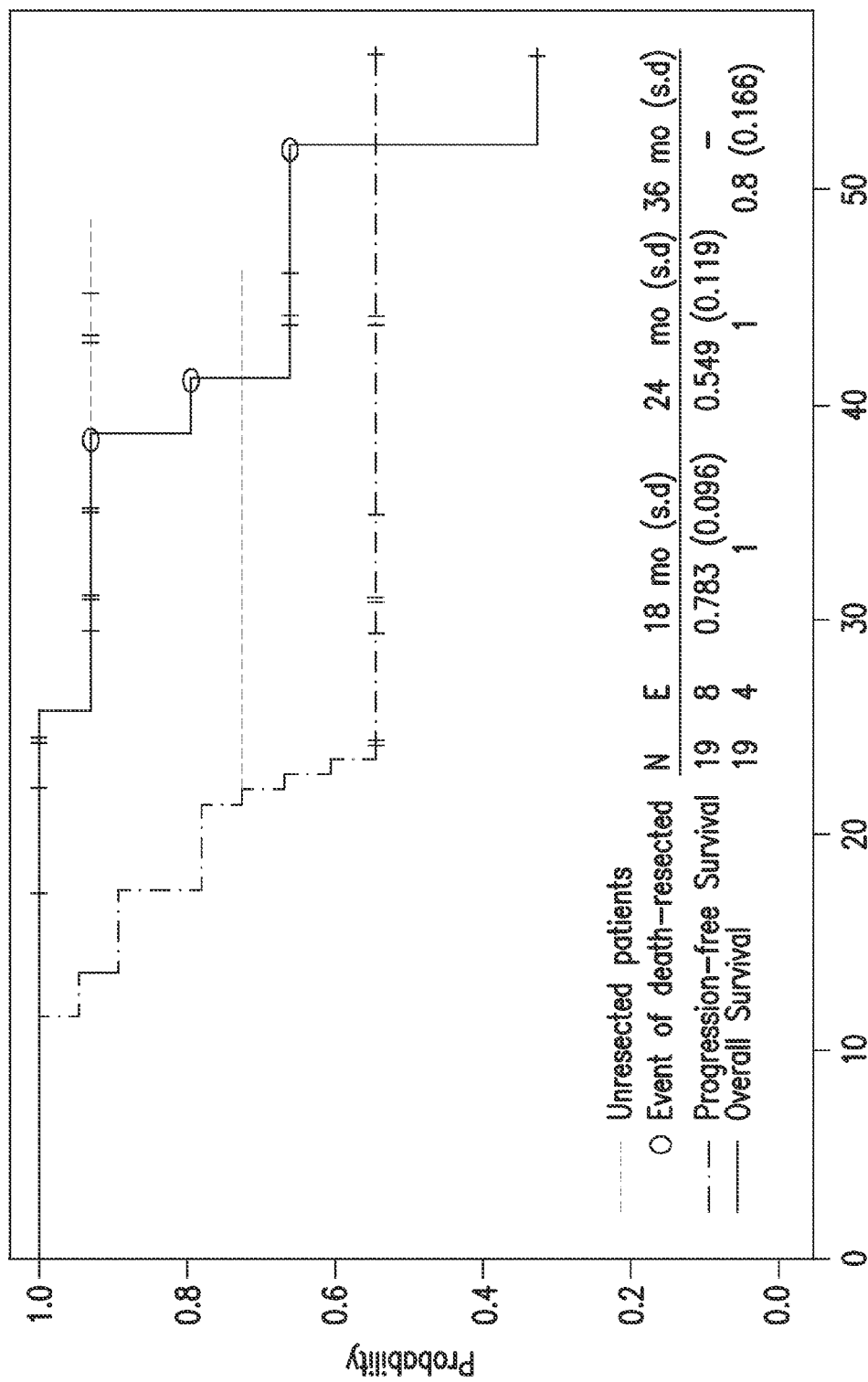
FIG. 7: Progression free survival and overall survival in resected and unresected patients (n=19) (study 2).

Five-year PFS from XCEL was 57% and 71% for all patients and none-surgical group, respectively. Five patients remained on XCEL with longest at 43+ months (FIG. 5). Five-year OS was 64% and 92% for all patients and none-surgical patients respectively (FIG. 7) The median OS was reached at 54 months for all patients because of three deaths in the surgical group. Only one unresected CR patient with solitary peritoneal metastasis died at 24 months since she refused additional therapy after she discontinued after 6 months of XCEL following XCEL plus radiation. The median time to relapse from CR date was 14 months (95% CI, 6-17 months). All eight relapse (41%) occurred at original sites (except for resected patients) equally split between the unresected patients (29%) versus the resected patients (67%) The subsequent treatment was summarized occurring primarily in the resected patients Table 2. The fact that resected patients had bulkier tumors (8-15 cm) and only one CR to XCEL may in part explain the high rate of relapse and death in this group. Interestingly, those patients with positive margin resection have proceeded adjuvant XCEL are still alive as compared to those with positive margins.

Toxicities

Despite the fact that the median duration of XCEL was 12 months (range, 1.8-43 months), the most common reason for discontinuing XCEL was CR from treatment or surgery (n=8) and two discontinued celecoxib for grade 2 agitations and two for late grade 1 elevation in serum creatinine. Similar to the prior report, the most common and one and only grade ¾ toxicity was lymphopenia (28%) of unknown clinical significance. Most common grade ½ toxicity was diarrhea (44%) followed by HFS (28%). Unexplained mild weight gain (n=2) and osteoporosis (n=1) was suspected. Hematologic toxicities were limited to grade 1 neutropenia and thrombocytopenia. Median increases in mean corpuscular volume (MCV) before and after XCEL treatment was 10 (range 5-20) as compared to MCV of −2 in that none-compliant patient.

High rate of sustainable CR was achieved with XCEL integrating multimodality therapy, leading to an unprecedented five year survival in selected colorectal cancer patients with hepatic only as well as extrahepatic metastases despite many unfavorable tumor characteristics. Surprisingly, five-year PFS (70%) and OS (92%) for the unresected CR patients exceeded the historical controls in patients with most favorable resectable liver-only metastasis (Fong et al., 1999; Taieb et al., 2005). Survival for the six resected patients were also favorable since three of six patients had R1 resections (Abdalla et al., 2004). The current study is small and retrospective, but represents a unplanned exhaustive subset of patients, whose prolonged survival was also consistently found for patients who took XCEL in either first-line or second-line settings. The study does not define the role of celecoxib in the survival outcome given that 13 patients (62%) had chemo-radiation and 9 patients (47%) were first-line responders. Until XCEL is validated in prospective study, patients with resectable colorectal cancer metastasis should undergo curative resection when feasible (Fong, 2000; Topham and Adam, 2002; Abdalla et al., 2004; Adam et al., 2001; Kemeny et al., 1999). However, the conventional view that radiation plays only palliative role is challenged by this study especially in those with retroperitoneal nodal metastasis, where the CR rate of 50% was achieved. Progressive disease in these nerve-rich retroperitoneal nodal regions can be detrimental to quality of life.

Following first-line response or chemo-radiation with XCEL or after surgery, XCEL was continued in patients to inhibit the tumor regrowth, leading to CR rate of 90% in first-line responders and sustained CR rate of 70% in the unresected patients. This high rate of CR could have been the sole results of first-line therapy (as there were no CR) and would only be feasible by the sums pathological CR rate (6-30%) and rate of microscopic tumor (20-30%) expected in patients with locally advanced rectal cancer treated with chemoradiation (Lin et al., 2005; Kim et al., 2005). Even though only one patient had confirmed pathological CR (5%) in both liver and in the irradiated rectum, no other CR patient had gone to surgery. Interestingly, six (43%) of 14 patients (including 9 patients with multifocal metastasis) who discontinued XCEL remained in CR at a median follow-up of 36 months, implying the pathological CR rate in this study may be above 5%. In addition, continuation of XCEL after attaining CR in 15 patients would have suppressed the regrowth of microscopic tumor since all relapses occurred following XCEL discontinuation at the initial tumor sites after a median time of 14 months (95% CI, 6-17 months), sufficient for a microscopic tumor to become detectable radiographically at a reported median linear growth rate of 0.083 mm/day (0.008-0.262 mm/day) or median volume doubling time of 130 days (53-1570 days) for colorectal cancer (Bolin et al., 1983).

CR as a result of suppressing microscopic tumor cells from regrowth is reminiscent of tumor dormancy model following prolonged antiangiogenic or metronomic treatment in animal models (O'Reilly et al., 1997; O'Reilly et al., 1996). It lends support to the claim that XCEL may be anti-angiogenic fortuitously followed a metronomic dosing paradigm (Browder et al., 2000; Kerbel and Kamen, 2004). Moreover, one of putative targets of tumor angiogenesis is bone marrow derived circulating endothelial progenitor (CEP), virtually indistinguishable by surface markers from hematopoietic stem cells (HSC) characterized by CD34 and CD133 expression (Lyden et al., 2001; Peichev et al., 2000). Low dose metronomic cyclophosphamide results in normalization of CEP, whereas high dose cyclophosphamide at maximal tolerated dose mobilizes viable CEP consistent with finding in patients with breast cancer patients receiving adjuvant chemotherapy (Bertolini et al., 2003; Furstenberger et al., 2006). Response of combining intermittent cyclophosphamide with metronomic cyclophosphamide produced most durable tumor response than metronomic chemotherapy (Shaked, 2005). CEP levels measured by flow cytometry or by CD133 mRNA are elevated in human cancers and correlated with cancer progression (Mancuso et al., 2003; Lin et al., 2002). Reduction or normalization of CEP levels correlated with response to antiangiogenic therapy (Willett et al., 2004). The inventors suspect that elevated MCV (Sussman et al., 2003), minimal myelosuppresion but profound lymphopenia may be more than a bystander's effect on HSC but a direct or indirect effects on CEP mobilization (Furstenberger et al., 2006). Conversely, the number and function of CEP correlate inversely with cardiovascular risk factors, and independently predict cardiovascular events and death (Hill et al., 2003; Werner et al., 2005), potentially explaining the increased cardiovascular events from anticancer therapies.[4]

In addition to cardiac and renal toxicities concern from celecoxib Lin et al., 2005), the inventors observed unexplained modest weight gain (n=2) and grade 1 osteoporosis (n=1) in patient who took XCEL over 24 months. Even though XCEL was continued beyond 12 months in 70% of the patients, the overall toxicities profiles were favorable. Continuing maintenance XCEL beyond CR may result in overtreating 10-30% of patients on chemoradiation or 1-5% of the patients on chemotherapy, assuming these patients may have achieved complete pathological CR in both gross and microscopic tumors. Since XCEL is orally self-administered, one patient later admitted none-compliance, whose peak MCV increase before and after XCEL was −2 compared to a mean+ 10 in the compliant patients. Serial MCV may be used as a surrogate of capecitabine compliance (Sussman et al., 2003).

In summary, XCEL resulted in unprecedented sustained CR rate, PFS and OS in selected patients with metastatic colorectal cancer, converting a sub-acute disease to a chronic one. The fact that XCEL is all-oral, safe, and inexpensive, and may be broadly applicable to all first-line responders may have far reaching implications since the newer first-line chemotherapies with targeted agents are expensive and did not improve CR rate despite improved response rate up to 80% Hurwitz et al., 2004; Diaz Rubio et al., 2005; Hochster, 2006). CR was also feasible with XCEL in patients who responded to first-line oxaliplatin combination. Studies with metronomic chemotherapy with or without selective COX-2 inhibitor so far had reported very modest antitumor activity because only patients who were heavily pretreated, or refractory to treatment were included without integration of radiation therapy (Werner et al., 2005; Shaked et al., 2005; Kieran et al., 2005; Spieth et al., 2003). Beyond the ongoing randomized phase III study to discern the effects of celecoxib on capecitabine induced hand-foot syndrome, the inventors intend to molecularly classify these CR patients beyond the clinical characteristics and to better understand mechanism of CR in relationship to tumor dormancy, and to optimize the dose and schedule duration of XCEL using CEP and other markers as a surrogate marker.

Example 5

Materials and Methods for Study 3

Patients

The institutional review board approved this study. All nineteen patients with unresectable metastatic colorectal cancer started XCEL (capecitabine 1000 mg/m2/day BID and celecoxib 200 mg PO BID) from February 2001 to November 2003. Eleven patients had first-line irinotecan with either 5FU or capecitabine and 8 patients took XCEL+radiation as first-line therapy. Six patients had negative margin (R0) or microscopic margin (R1) resections, one of which was pathological CR and two had gross positive margin (R2) resections prior to XCEL. All patients had clinical examinations, laboratory and CT scan every 2-3 months. Maintenance XCEL (extended adjuvant therapy) is defined as continuation of XCEL beyond radiologic or surgical CR (n=14).

Evaluation and Definitions

The principal investigator and two board-certified radiologists reviewed all the CT scan images. CR was defined according to the RECIST criteria as complete disappearance of measurable or none-measurable disease. Effective CR (eCR) was coined to describe normalization of an anatomical structure (e.g. nodes) that cannot regress completely. Confirmed CR included those patients who had CR by meeting the RECIST criteria or had achieved eCR or pathological CR. Near CR (nCR) were defined as almost complete disappearance (95-99%) of measurable disease on CT scan. Relapse free survival (RFS) was defined as the time from first radiologic CR to first recurrence, progression, or death. Progression free survival (PFS) time was defined as the time from the start of XCEL to recurrence, progression of measurable disease or death form any cause. OS was defined as the time from first radiologic CR to death from any cause. Treatment related toxicity was graded in accordance with the National Cancer Institute Common Toxicity Criteria for Adverse Events, version 3.0.

Statistical Analysis

Continuous variables were summarized using the median (range) and categorical variables were summarized in frequency tables. Patients were censored at the date of last follow-up if their disease had not progressed or if they had not died. The death date was ascertained by searching (ssdi.genealogy.rootsweb.com) using social security numbers or phone follow-up. Therefore, it was possible for censored OS times to be greater than censored RFS and PFS times. Kaplan-Meier estimates for RFS, PFS, and OS were calculated, and group comparisons made using log-rank tests. The analyzed prognostic and treatment factors include: maintenance therapy (yes or no), resections (unresected/R1-2 or R0), site (intrahepatic or extrahepatic), tumor size (>8 cm or less), metastasis number (single versus multifocal), initial stage on diagnosis (stage II or stage III/IV), disease free interval prior to stage IV disease (6 months or less), LDH prior to XCEL (normal versus abnormal), radiation (yes or no), and response to first-line irinotecan based treatment (yes or no).

Example 6

Effects of Combination Therapy Study 3

Patient Characteristics

Figure 9:
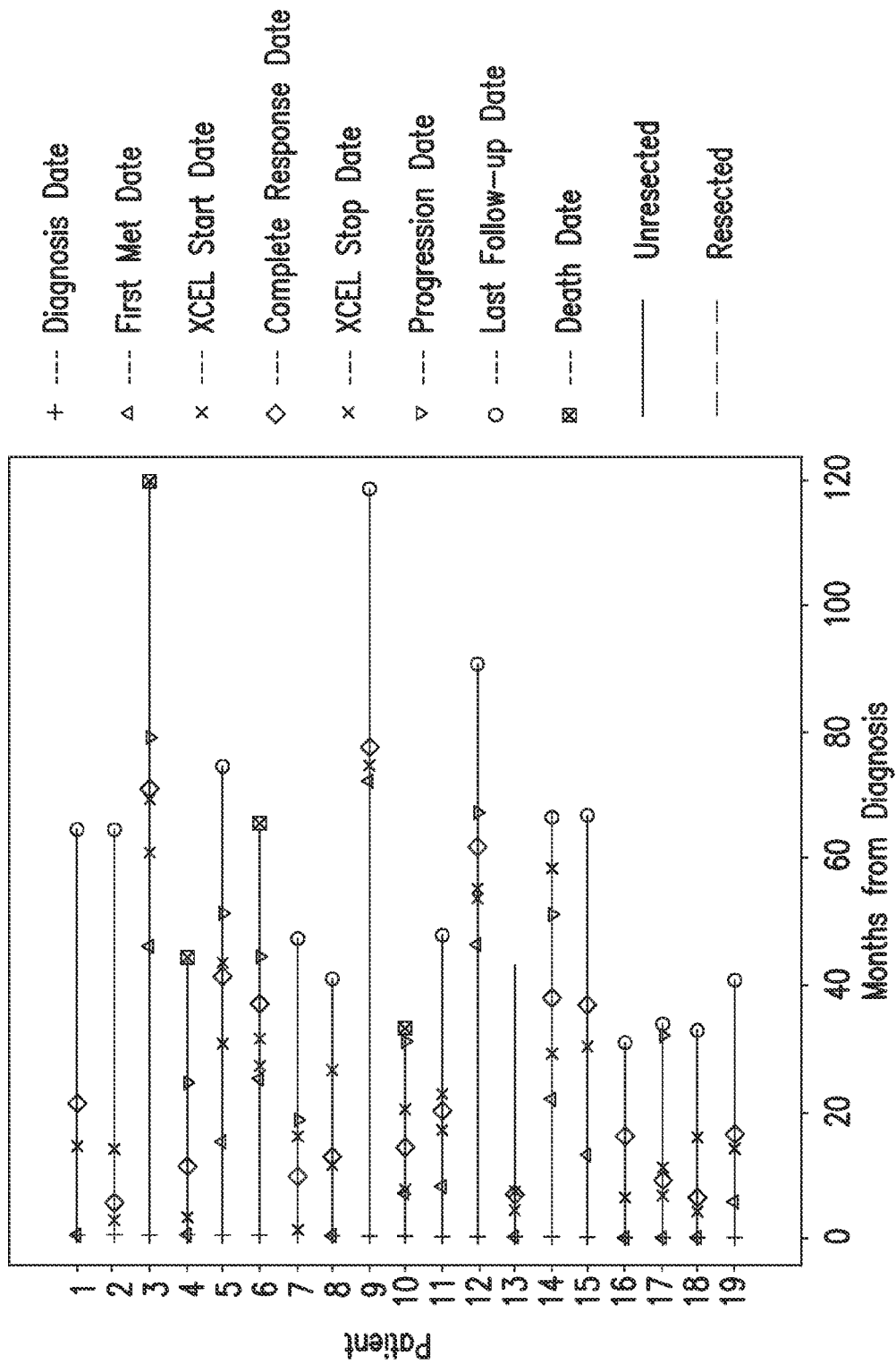
FIG. 9: Event chart analysis from diagnosis of colorectal cancer (study 3).

Patient demographics are summarized in Table 6. Detailed treatment and survival characteristics are shown in Table 7 and FIG. 9. All patients had either pathologic confirmation of metastasis (n=15) or elevated tumor marker and unequivocal radiographic evidence of metastasis (n=4). Poor prognostic factors included node positive primary or stage IV disease on presentation ($^{16}/_{19}$, 84%), extrahepatic disease ($^{13}/_{19}$, 68%), or multifocal disease ($^{10}/_{19}$, 53%), or tumor size >8 cm ($^{5}/_{16}$, 31%), resistance to first-line irinotecan based treatment ($^{3}/_{19}$, 16%). The favorable prognostic characteristics were normal levels of lactate dehydrogenase ($^{16}/_{19}$, 84%), carcinoma embryonic antigen level <200 ng/ml ($^{18}/_{19}$, 95%), responses to first-line therapy (11/19, 58%) and solitary metastasis (9/19, 47%). The median disease free interval before metastasis was 5.7 months (95% CI 3.9-23.5 months). Following downsizing with neoadjuvant chemotherapy with XCEL+radiation, five had R0 resections of the metastatic disease and one had a R1 resection and two had R2 resections prior to initiating therapy. The pathological findings were: one pathological CR, two microscopic residue disease, and five macroscopic disease. Twelve patients had radiotherapy (35-50.4 Gy) with XCEL and eight were responding to first-line irinotecan regimens.

TABLE 6

Baseline Patient, Disease, and Treatment Characteristics (n = 19)

| Category | No. of patients (%) |
|---|---|
| Median age (range) | 62 (30-82 years) |
| Sex | |
| Male | 13 (68) |
| Female | 6 (32) |
| Race | |
| White | 19 (100) |
| Eastern Cooperative Oncology Group (ECOG) performnce status | |
| 0 | 10 (53) |
| 1 | 8 (42) |
| 2 | 1 (5) |
| Primary colon cancer | 12 (64) |
| Primary rectal cancer | 7 (36) |
| Inital AJCC Stages | |
| II | 3 (16) |
| III | 7 (37) |

TABLE 6-continued

Baseline Patient, Disease, and Treatment Characteristics (n = 19)

| Category | No. of patients (%) |
|---|---|
| IV | 9 (47) |
| Median time to stage IV disease (months) | 5.9 (0-73) |
| Median size (centimeter n = 16) | 3 (0.8-15) |
| Solitary metastasis | 9 (47) |
| Node[†] | 3 (16) |
| Liver[††] | 2 (11) |
| Peritoneum | 2 (11) |
| Lung | 1 (5) |
| Pelvis | 1 (5) |
| None-solotary metastasis | 10 (53) |
| Median number of metastasis (range) | 4 (2-9) |
| Liver | 4 (22) |
| Liver-lung | 2 (11) |
| Carcinomatosis | 2 (11) |
| Lung | 1 (5) |
| Elevated CEA > 3.0 ng/ml (range 3-2250) | 10 (53) |
| Elevated CA19.9 | 1 (5) |
| Radiation | |
| ≥45 Gy | 9 (47) |
| <45 Gy | 3 (16) |
| None | 7 (37) |
| Firstline XCEL | 8 (42) |
| First-line Irinotecan | 11 (58) |
| Post-XCEL R0-1 resections | 6 (32) |
| Pelvis | 2 (11) |
| Liver[††] | 3 (16) |
| Lung | 2 (6) |

[†]Three patients had clustered nodal metastases
[††]One patient with synchronous rectal primary and liver metastasis

TABLE 7

Summary of the tumor characteristics and survival from XCEL and pattern of relapse.

| No. | Age/Sex | Tumor site(s) | Size (cm) | Tumer Number | First-line Treatment | RT (GY) | Independent review f[resections R0-2] | Maintenance XCEL | RFC from OR months | OS item net | Relapse/Death | Subsequent Treatments |
|---|---|---|---|---|---|---|---|---|---|---|---|---|
| 1 | 60 M | Aortocaval node | 3.6 | 1 | IFL | 36 | aCR | yes | 43.2 | 63.5 | No | |
| 2 | 62 F | Pelvis | 6 | 1 | XCEL | 39 | SD (R1) | yes | 54.2 | 60.0 | No | |
| 3 | 45 F | Right lung | 2 | 1 | XCEL | — | SD (R1) | no | 20.3 | 78.4 | Yes/Yes | IRI, FOLFOX, |
| 4 | 51 F | Liver | 8 | 2 | IROX | 50.4 | PR (P0) | no | 13.4 | 44.3 | Yes/Yes | XCEL, As six agents |
| 5 | 76 M | Liver | 3 | 1 | XCEL | 00.4 | nCR | yes | 10.1 | 59.6 | Yes/No | RFA to liver |
| 6 | 82 M | Lung | 8 | 3 | XCEL | 40 | PR (R0) | no | 7.3 | 40.2 | Yes/Yes | XELRI.FOLFOX |
| 7 | 64 M | Liver | 15 | 3 | XCEL | 45 | PR (R0) | yes | 8.9 | 45.0 | Yes/No | All six agents, XCEL + RT |
| 8 | 53 M | Liver | 1.6 | 9 | IFL; XELIRI | — | CR | yes | 40.1 | 40.1 | No | |
| 9 | 76 M | Small bowel | NA | 1 | XCEL | — | Unconfirmed [R2] | yes | 41.4 | 52.7 | No | |
| 10 | 84 M | Peritoneal metastasis | 5 | 1 | XCEL | 50.4 | Unconfirmed | yes | 17 0 | 33.3 | Yes/Yes | None; patient's choice |
| 11 | 81 M | Mesenteric node | 3 | 1 | XCELIRI | 45 | CR | no | 26.1 | 47.0 | No | Lost for CT scan but not survival |
| 12 | 70 M | Inguinal node | 3 | 1 | XCEL | 45 | Unconfirmed | yes | 6.6 | 47.0 | Yes/No | RTA to inguinal node |
| 13 | 30 M | Liver and rectum | 8.5 | 1 | IFL | 45 | nCR (R0) | yes | 38.0 | 44.3 | No | |
| 14 | 54 M | Gastrohepatic nodes | 2.2 | >6 | XELIRI | 50.4 | nCR | yes | 13.1 | 42.3 | Yes/No | XCEL + RT, IRI only |
| 15 | 36 F | Para-arotic nodes | 2.6 | 4 | IFL | 50.4 | aCR | yes | 31.6 | 54.9 | No | |
| 16 | 52 F | Liver | 3 | 4 | XELIRI | — | CR | yes | 18.7 | 34.6 | No | |
| 17 | 67 M | Carcinomatosis | NA | >2 | XELIRI | — | Unconfirmed [R2] | yes | 27.6 | 38.3 | Yes/No | |

TABLE 7-continued

Summary of the tumor characteristics and survival from XCEL and pattern of relapse.

| No. | Age/Sex | Tumor site(s) | Size (cm) | Tumer Number | First-line Treatment | RT (GY) | Independent review f[resections R0-2] | Maintenance XCEL | RFC from OR months | OS item net | Relapse/Death | Subsequent Treatments |
|---|---|---|---|---|---|---|---|---|---|---|---|---|
| 18 | 75 M | Liver and lung | 6.8 | 6 | XELIRI | — | CR | yes | 27.0 | 33.1 | No | |
| 19 | 64 F | Para-arotic nodes | 2.6 | 1† | IRI | 50.4 | aCR | | 25.1 | 35.3 | No | |

†Atleast 3-4 clusters nodal metastasis,
pCR = pathological complex response,
eCR = effective CR,
nCR = near,
PR = partial responce
SD = stable disease.
PD = progressive disease.
NA = not evaluable
RT = Radition therapy,
XELIRI = capecitabine and irinotecan.

Complete Response

All nineteen patients had at least one report indicating no radiographic evidence of disease agreed by one of two independent radiological reviews. The second independent review was also able to verify the radiological findings in all but 4 of 19 patients. The confirmed CR patients included 1 pathologic CR patient, 3 eCR, 4 CR and 7 surgically resected patients (4 R0 resections, 1 R1 resection and 2 R2 resections). Interestingly, the pathological CR occurred in a patient with a solitary liver metastasis that did not completely regress radiographically. Four unconfirmed CR patients were only evident retrospectively with two patients whose respective inguinal node or peritoneal mass could not be distinguished from post radiation changes; and in two near CR patients. One near CR patient was found to have a residue 1.2 cm gastro-hepatic node among diffuse abdominal nodes (>3 cm) regressed to sub-centimeter nodes following chemoradiation. The other near CR patient had solitary liver metastasis had regressed from 3 cm to 2 mm following radiotherapy plus XCEL (Table 7). All patients with elevated serum carcinoma embryonic antigen (CEA) or elevated CA19.9 levels had their CEA or CA19.9 normalized during CR.

RFS

Nine patients relapsed during the follow-up at 5 to 27 months following CR. Two-year RFS was 57% (Table 8). The median RFS was not reached (95% Confidence Interval [CI], 17 months—[NR] not reached) Paradoxically, two-year RFS was 71% (95% CI, 0.51-1.00) for the 14 unresected and R1-2 resected patients versus 20% (95% CI, 0.03-1.00) for the five R0 resected patients, one of whom was a pathologic CR patient (p=0.07), or versus 0% excluding the one pathological CR patient (p=0.015). Two-year RFS estimate was 73% (95% CI, 0.54 to 1.00) for the maintenance XCEL group versus 0% without maintenance XCEL (p=0.002) (FIG. 10A.). Other prognostic and treatment factors did not predict RFS (Table 8). Consistent with the other report, all relapses occurred exclusively in situ except for the resected patients following discontinuing or not initiating maintenance XCEL after CR. Among nine relapses, five were retreated with XCEL alone or with radiation, two had radiofrequency ablation, and one had resection at the anastomosis site indicating the nature of in situ relapses. A sensitivity analysis calculated the log-rank tests reported in Table 8 using a dataset excluding the 4 patients with unconfirmed CR. The results were similar for predicting both RFS and OS, with an exaggeration of the RFS (p=0.0005) advantage for not achieving R0 resections. A paradoxical PFS advantage in the unresected and R1-2 resected patients (p=0.069) and in patients who received maintenance XCEL (p=0.002) was also observed.

TABLE 8

Time to event analysis for relapse free survival (RFS) and overall survival (OS), n = 19.

| | | E/N | 2-year RFS (95% CI) | P-value* | E/N | 3-year OS (95% CI) | P-value* |
|---|---|---|---|---|---|---|---|
| All patients | | 9/19 | 0.57 (0.39, 0.85) | | 4/19 | 0.79 (0.59, 1.00) | |
| Maintenance XCEL | yes | 5/15 | 0 73 (0 54, 1.00) | .002 | 1/15 | 0 93 (0.82, 1.00) | .04 |
| | no | 4/4 | 0.00 | | 3/4 | 0.38 (0.08, 1.00) | |
| Metastectomy | none/R1-2 | 5/14 | 0.71 (0.51, 0.99) | .07 | 1/14 | 0.60 (0.80, 1.00) | .13 |
| | R0 | 4/5 | 0.20 (0.03, 1.00) | | 3/5 | 0.60 (0.29, 1.00) | |
| Extrahepatic | yes | 6/13 | 0.50 (.20, 1.00) | .12 | 3/13 | 0.67 (0.55, 1.00) | .60 |
| | no | 3/6 | 0.52 (0.15, 1.00) | | 1/6 | 0.79 (0.66, 1.00) | |
| Tumor size | <8 cm | 4/11 | 0.62 (0.39, 1.00) | .35 | 1/11 | 1.00 | .46 |
| | ≥8 cm | 3/5 | 0.40 (0.14, 1.00) | | 2/5 | 0.60 (0.29, 1.00) | |
| Metastatic Number | solitary | 4/9 | 0.56 (0.31, 1.00) | .71 | 2/9 | 0.89 (0.71, 1.00) | .42 |
| | non-solitary | 5/10 | 0.60 (0.36, 1.00) | | 2/10 | 0.60 (0 29, 1.00) | |
| Stage at Diagnosis | II/III | 6/10 | 0.40 (0.19, 0.85) | .22 | 3/10 | 0.77 (0.53, 1.00) | .30 |
| | IV | 3/9 | 0.78 (0.55, 1.00) | | 1/9 | 0.83 (0.58, 1.00) | |
| Disease-free interval prior To metastasis | <6 mo | 3/10 | 0.64 (0 44, 1.00) | .10 | 1/10 | 0.75 (0.54, 1.00) | .19 |
| | ≥6 mo | 6/9 | 0.50 (0.28, 0.88) | | 3/9 | 0.74 (0.39, 1.00) | |
| LDH | Abnormal | 3/3 | 0.33 (0.07, 1.00) | .08 | 1/3 | 0.50 (0.13, 1.00) | .45 |
| | Normal | 6/16 | 0.62 (0.42, 0.91) | | 3/16 | 0.85 (0.68, 1.00) | |
| Radiation | yes | 6/12 | 0.50 (0.28, 0.88) | .68 | 2/12 | 0.79 (0.56, 1.00) | .58 |
| | no | 3/7 | 0.69 (1.40, 1.00) | | 2/7 | 0.75 (0.43, 1.00) | |

TABLE 8-continued

Time to event analysis for relapse free survival (RFS) and overall survival (OS), n = 19.

|  |  | E/N | 2-year RFS (95% CI) | P-value* | E/N | 3-year OS (95% CI) | P-value* |
|---|---|---|---|---|---|---|---|
| Response to first-line therapy | yes | 3/9 | 0.58 (0.39, 1.00) | .28 | 0/9 | 1.00 | .15 |
|  | no | 6/10 | 0.40 (0.25, 1.00) |  | 4/10 | 0.65 (0.49, 1.00) |  |

E = number of events in category;
N = number of potients in category;
CI = confidence interval
*log-rank test

OS

Four patients died during follow-up including 3 R0 resected patients who did not receive any maintenance therapy and 1 unconfirmed CR patient who elected no further therapy after eight months of maintenance XCEL. The estimated 3-year survival rate from CR and from diagnosis was 79% (95% CI, 0.59-1.00) and 95% (95% CI, 0.85-1.00) respectively. The median OS from XCEL and from onset of metastasis reached 51.9 months (95% CI, 45 months—not reached [NR]) and 73.3 months (95% CI, NR-NR months) respectively. Improved OS was associated with maintenance XCEL (p=0.04) (FIG. 10B), reaching a four year OS of 93% from CR but not with any other prognostic or treatment factors (Table 8).

Toxicities

Figure 8:
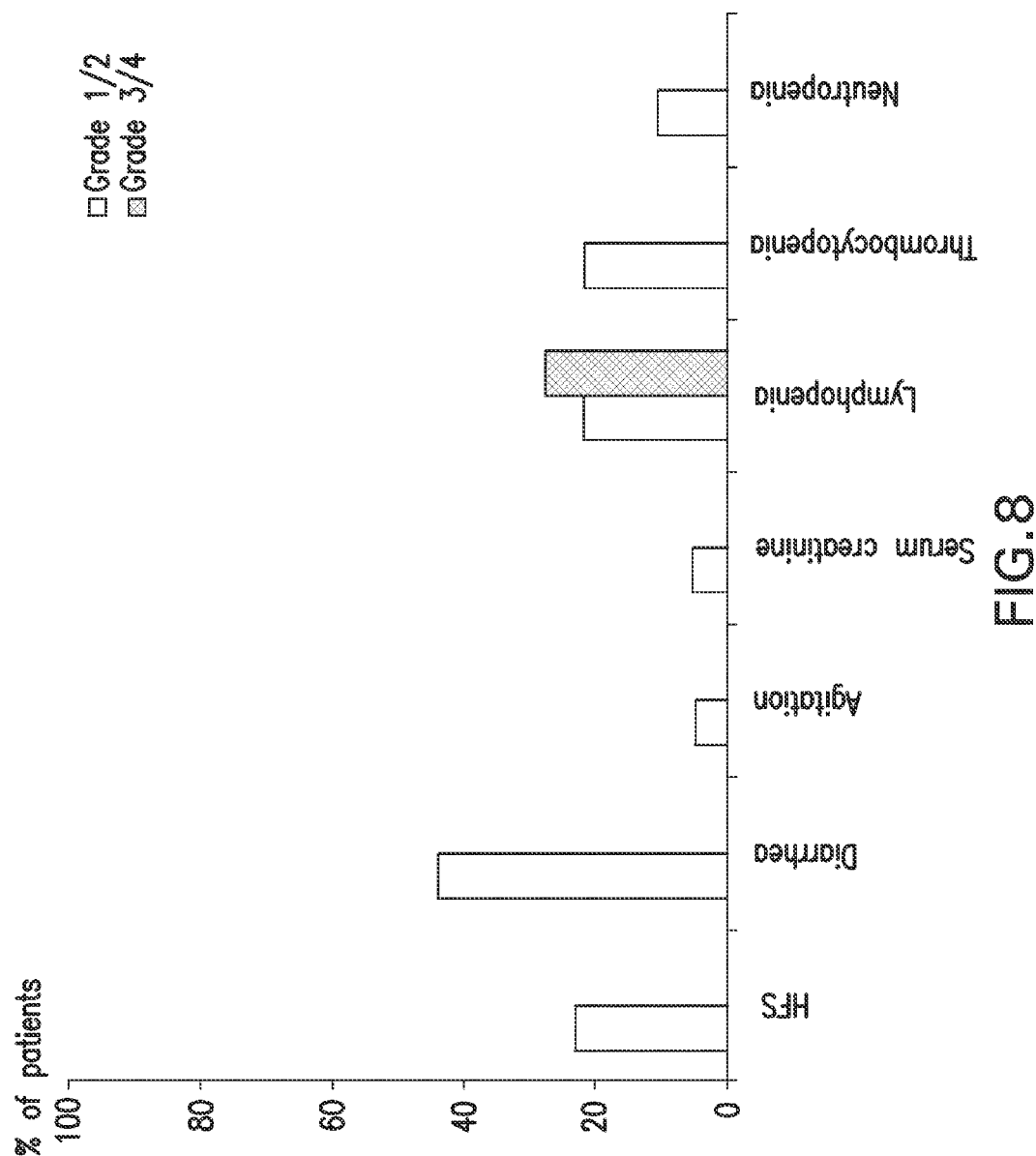
FIG. 8: Attributable adverse events (study 2).

The toxicities were very similar to the previous report (results identical to FIG. 8).18 One patient discontinued celecoxib after two years of XCEL due to a grade 1 elevated serum creatinine. Median mean corpuscular volume (MCV) increase from baseline after XCEL was 11.5 (95% CI, 8-14). No cardiovascular toxicities were encountered in this group and all patients who had received XCEL for 12 months or more also received 81 mg aspirin daily.

Discussion

Maintenance XCEL, but not any other measured prognostic or treatment factors conferred survival advantage. One may attribute this effect due to a difference in CR, as confirmed CR patients enjoyed a 3-year PFS of 100% versus 0% with unconfirmed CR patients versus 37% for the R0-2 resected patients. Interestingly, five of eight none-surgical CR patients continued maintenance XCEL beyond 24 months (range 27-50.3 months), in contrast, unconfirmed CR patients either did not receive or had less than 6 months of maintenance XCEL. The observations were incidental and the analysis was based on exclusively all "CR" patients from the XCEL database from October 2000 through November 2003. The magnitude of survival even with the selection bias was nonetheless provocative and the RFS and OS among R0-1 resected patients were consistent with the historical controls. Even though this study includes only 19 patients, a statistical significant difference in RFS and OS emerged for those patients who took maintenance XCEL by univariate log rank analysis.

Maintenance XCEL is hypothesized to target colorectal cancer micrometastases, as no patient relapsed while on XCEL. All 9 relapses occurred in situ, except for the four R0 resected cases, consistent with other reports that majority (84%) of CR patients relapsed in situ within the first year. The median time from CR to relapse in the current study was 13.1 months, a time sufficient for micrometastases to become radiographically detectable at a median linear growth rate of 0.083 mm/day (range 0.008-0.262 mm/day) reported for colorectal cancer. Among the resected patients following neoadjuvant XCEL plus radiation, we found one had a pathological CR and two had microscopic residue disease, these findings reminiscent of the patients with LARC treated with chemoradiation. Occasionally, microscopic disease or pathological CR was also seen in patients with metastatic colorectal cancer responding to combination chemotherapy. Eight of nine first-line irinotecan responders had achieved CR (88%) with XCEL alone or with radiation, a rate achievable only by combining the rate of microscopic residue disease and rate of pathological CR. The pathological CR rate is not known, but may be higher than the observed 5% (1/19), as 14 patients did not have resections and the 3 year RFS had reach 57% for the whole cohorts. Expanded clinical experience suggests that maintenance XCEL following CR appeared be reproducible with other first line combination chemotherapy. Effectively targeting colorectal cancer micrometastases with maintenance XCEL led to durable clinical CR, a finding similar to the tumor dormancy models, in which tumor xenografts would regress to a dormant.

Example 7

Analysis of CD133 Expression in Patient Samples

The serum CD133 mRNA levels were determined for patients who received XCEL therapy. In each case, CD133 serum mRNA levels were determined by RT-PCR and all values were normalized to the GAPDH expression levels from the sample (see, e.g., Iinuma et al., 2011). The results of these studies are shown below in Table 9. As of Jan. 1, 2012 all patients indicated by "*" remain living. Accordingly these patients display an extended period of remission in some cases exceeding 10 years. Notably, the surviving patients all displayed very low serum CD133 RNA levels. In fact, excluding the patient indicated by % (this patient had not received therapy prior to blood sampling), all CD133 RNA levels were less than 1.0 (as normalized to GAPDH), meaning that fewer copies of CD133 transcript were present than GAPDH transcript. Average CD133 RNA levels for patients that had recurrence was over 1,000 (1,444.6215) and average CD133 RNA level for patients indicated by an "*" was 0.3381 (excluding patient 42). Thus, these exceedingly low CD133 levels are predictive of a complete response and an absence of disease relapse.

TABLE 9

CD133 mRNA levels in patients with complete response

| SL._NO | BW_ID | AGE | DATE_DIA | DATE_BLO | MEAN_DIF |
|---|---|---|---|---|---|
| 54 | BW7918 | 75 | Aug. 11, 2001 | Feb. 12, 2003 | 3997.83 |
| 44 | BW7317 | 63 | Aug. 18, 2000 | Jul. 31, 2002 | 5.17 |
| 17 | BW6959 | 71 | Jan. 18, 2002 | Apr. 29, 2002 | 0.029 |

TABLE 9-continued

CD133 mRNA levels in patients with complete response

| SL._NO | BW_ID | AGE | DATE_DIA | DATE_BLO | MEAN_DIF |
|---|---|---|---|---|---|
| 62 | BW8132 | 86 | Dec. 23, 2002 | Mar. 27, 2003 | 6.08 |
| 4 | BW6764 | 87 | Dec. 7, 2001 | Mar. 15, 2002 | 0.000049 |
| 59 | BW8002 | 32 | Apr. 24, 1995 | Feb. 26, 2003 | 0.035 |
| 35 | BW7161 | 56 | Nov. 6, 1995 | Jun. 24, 2002 | 0.017 |
| 28 | BW7065 | 67 | May 28, 1994 | May 15, 2002 | 0.000000005 |
| 38 | BW7197 | 57 | Dec. 27, 1996 | Jul. 3, 2002 | 2.11 |
| 78 | BW8727 | 59 | Mar. 17, 1998 | Aug. 11, 2003 | 3.85 |
| 18 | BW6968 | 52 | Dec. 23, 1998 | May 1, 2002 | 0.18 |
| 45 | BW7322 | 59 | Mar. 18, 1998 | Jul. 31, 2002 | 0.13 |
| 6 | BW6810 | 41 | Jun. 1, 1999 | Mar. 27, 2002 | 374.81 |
| 22 | BW7005 | 80 | May 2, 2000 | May 8, 2002 | 0.00061 |
| 20 | BW6985 | 61 | Jun. 1, 2000 | May 7, 2002 | 0.12 |
| 12 | BW6920 | 65 | Mar. 23, 1998 | Apr. 18, 2002 | 28.74 |
| 39 | BW7214 | 54 | Oct. 10, 2000 | Jul. 3, 2002 | 12.34 |
| 43 | BW7272 | 69 | Aug. 28, 2000 | Jul. 31, 2002 | 1.09 |
| 49 | BW7429 | 46 | Sep. 19, 2000 | Sep. 11, 2002 | 3.2 |
| 11 | BW6900 | 81 | Apr. 18, 2000 | Apr. 17, 2002 | 0.0011 |
| 64 | BW8168 | 48 | Dec. 18, 2000 | Apr. 2, 2003 | 0.028 |
| 61* | BW8129 | 70 | Nov. 17, 2000 | Mar. 27, 2003 | 0.56 |
| 32 | BW7105 | 49 | Sep. 1, 1999 | Jun. 12, 2002 | 0.015 |
| 8 | BW6825 | 73 | Dec. 5, 2000 | Apr. 1, 2002 | 106.89 |
| 7 | BW6824 | 51 | Jan. 11, 2000 | Mar. 27, 2002 | 0.082 |
| 66 | BW8223 | 55 | Mar. 19, 2001 | Apr. 16, 2003 | 0.17 |
| 42*, % | BW7271 | 69 | Mar. 4, 2001 | Jul. 17, 2002 | 2.96 |
| 15 | BW6945 | 72 | Mar. 26, 2001 | Apr. 24, 2002 | 4656.4 |
| 83 | BW9006 | 70 | Mar. 23, 1999 | Oct. 6, 2003 | 9.03 |
| 41 | BW7270 | 66 | Jun. 4, 2000 | Jul. 17, 2002 | 4.79 |
| 87 | BW9276 | 76 | Jun. 12, 2001 | Dec. 8, 2003 | 0.037 |
| 55* | BW7919 | 55 | Jun. 14, 2001 | Feb. 20, 2003 | 0.5 |
| 34 | BW7160 | 42 | May 12, 2001 | Jun. 12, 2002 | 0.00043 |
| 50 | | 51 | Jun. 16, 2001 | Sep. 11, 2002 | |
| 89 | BW9277 | 72 | Sep. 28, 2001 | Dec. 8, 2003 | 0.072 |
| 33 | BW7136 | 69 | May 30, 2001 | Jun. 12, 2002 | 0.000056 |
| 1 | BW6716 | 69 | Jan. 10, 2002 | Feb. 25, 2002 | |
| 2 | BW6756 | 55 | Jan. 4, 2002 | Mar. 15, 2002 | |
| 3 | BW6757 | 58 | Jan. 28, 2002 | Mar. 15, 2002 | |
| 27 | BW7064 | 74 | Mar. 7, 2002 | May 15, 2002 | 0.000089 |
| 26 | BW7022 | 60 | Mar. 12, 2002 | May 15, 2002 | 0.0014 |
| 9 | BW6898 | 55 | Aug. 10, 1993 | Apr. 1, 2002 | 7.36 |
| 21 | BW6990 | 64 | Sep. 13, 2001 | May 7, 2002 | 0.017 |
| 13 | BW6926 | 72 | Apr. 30, 1999 | Apr. 18, 2002 | 15662.21 |
| 10 | BW6899 | 45 | Feb. 22, 2002 | Apr. 17, 2002 | 0.0017 |
| 14 | BW6944 | 75 | Feb. 12, 2002 | Apr. 22, 2002 | 0.49 |
| 19 | BW6970 | 56 | Mar. 27, 2002 | May 1, 2002 | 0.0000084 |
| 16 | BW6958 | 55 | Mar. 18, 2002 | Apr. 29, 2002 | 0.015 |
| 23 | BW7018 | 60 | Apr. 3, 2002 | May 8, 2002 | 0.00044 |
| 24 | BW7020 | 67 | Apr. 11, 2002 | May 14, 2002 | 0.000089 |
| 25 | BW7021 | 49 | Apr. 1, 2002 | May 15, 2002 | 0.000000072 |
| 31 | BW7104 | 64 | Mar. 1, 2001 | Jun. 12, 2002 | 188.05 |
| 29 | BW7093 | 47 | Apr. 1, 2002 | Jun. 4, 2002 | 0.000003 |
| 82 | BW8982 | 71 | May 17, 2002 | Oct. 1, 2003 | 0.078 |
| 30 | BW7103 | 57 | Apr. 16, 2002 | Jun. 4, 2002 | 0.0000076 |
| 37 | BW7174 | 44 | May 3, 2001 | Jul. 1, 2002 | 0.0016 |
| 86 | BW9196 | 79 | Apr. 8, 2002 | Nov. 17, 2003 | 2.61 |
| 36 | BW7173 | 27 | Apr. 22, 2002 | Jul. 1, 2002 | 0.015 |
| 40 | BW7215 | 39 | May 30, 2002 | Jul. 10, 2002 | 3.66 |
| 84 | BW9020 | 65 | Jul. 31, 2002 | Oct. 8, 2003 | 0.092 |
| 47 | BW7409 | 61 | Jun. 19, 2002 | Aug. 12, 2002 | 9.35 |
| 46 | BW7372 | 47 | Jun. 20, 2002 | Aug. 12, 2002 | 9.82 |
| 48 | BW7410 | 43 | Jun. 13, 2002 | Aug. 30, 2002 | 83240.61 |
| 51 | | 46 | Nov. 26, 2001 | Sep. 11, 2002 | |
| 52 | | 70 | Oct. 13, 2000 | Feb. 3, 2003 | |
| 53 | BW7903 | 80 | Jan. 10, 1996 | Feb. 10, 2003 | 0.00048 |
| 58 | | 51 | Jan. 16, 2003 | Feb. 24, 2003 | |
| 56 | BW7965 | 88 | Dec. 16, 2002 | Feb. 20, 2003 | 0.12 |
| 57 | BW7977 | 67 | Feb. 6, 1999 | Feb. 24, 2003 | 1.52 |
| 60 | BW8084 | 52 | Mar. 29, 2001 | Mar. 17, 2003 | 0.0012 |
| 63 | | 64 | Dec. 31, 2002 | Apr. 2, 2003 | |
| 67 | BW8237 | 58 | Jan. 19, 2001 | May 21, 2003 | 1.14 |
| 65 | BW8196 | 62 | Feb. 4, 2003 | Apr. 9, 2003 | 0.94 |
| 68 | BW8328 | 53 | Apr. 15, 2003 | May 12, 2003 | 1.34 |
| 69* | BW8396 | 68 | Apr. 22, 2003 | May 28, 2003 | 0.29 |
| 70 | BW8420 | 59 | Apr. 8, 2003 | Jun. 4, 2003 | 0.0047 |
| 71 | BW8461 | 40 | May 10, 2003 | Jun. 11, 2003 | 0.89 |
| 72* | BW8519 | 64 | Oct. 9, 2002 | Jun. 25, 2003 | 0.0024 |
| 75 | BW8555 | 58 | May 24, 2003 | Aug. 4, 2003 | 0.46 |

TABLE 9-continued

CD133 mRNA levels in patients with complete response

| SL._NO | BW_ID | AGE | DATE_DIA | DATE_BLO | MEAN_DIF |
|---|---|---|---|---|---|
| 73 | BW8621 | 75 | Jul. 1, 2001 | Jul. 28, 2003 | 0.00006 |
| 74 | BW8683 | 35 | Jul. 1, 2003 | Jul. 30, 2003 | 0.00022 |
| 76 | BW8706 | 80 | Mar., 13, 2003 | Aug. 5, 2003 | 0.027 |
| 77 | | 66 | Jan. 24, 2003 | Aug. 6, 2003 | |
| 79 | BW8740 | 41 | Oct. 3, 2001 | Aug. 13, 2003 | 0.014 |
| 80 | BW8836 | 43 | Jul. 17, 2003 | Sep. 3, 2003 | 0.0063 |
| 81 | BW8969 | 60 | Aug. 15, 2003 | Sep. 29, 2003 | 0.22 |
| 85 | BW9170 | 68 | Oct. 14, 2003 | Nov. 10, 2003 | 0.21 |
| 88 | BW9278 | 51 | Nov. 10, 2003 | Dec. 8, 2003 | 0.16 |
| 90 | | 47 | Dec. 10, 2003 | Dec. 29, 2003 | |
| 91 | BW9346 | 55 | Sep. 15, 2003 | Dec. 29, 2003 | 1.93 |

*Indicates patients that were surviving as of January 2012; "DATE_DIA" indicates the date of diagnosis; "DATE_BLO" indicates the date of blood draw; "MEAN_DIF" indicates the CD133 RNA level (normalized to GAPDH) in the blood samples as determined by RT-PCT.
% Indicates that the subject had not yet received therapy when the blood sample for CD133 level was taken.

Further studies were undertaken to quantify the level of CD133 in a second group of patients treated with XCEL therapy as described above. However, in this case, absolute mRNA copy number values were obtaining using real-time RT-PCR (Table 10). In some cases, these values were normalized to either of two housekeeping genes: GAPDH and GUSB (far right 4 columns). As can be seen in FIG. 11, the use of either GusB or GAPDH as the housekeeping gene for normalization produced essentially equivalent results. Importantly, in these analyses, all patient showing compete response had serum CD133 RNA levels that were significantly lower, not only than that of cancer patients with disease recurrence, but also than the levels observed in healthy cancer-free subjects.

TABLE 10

CD133 mRNA levels in complete responders and healthy controls

| | RAW COPY NUMBER | | | NORMALIZED COPY NUMBER | | NORMALIZED COPY NUMBER × 100 | |
|---|---|---|---|---|---|---|---|
| | CD133 | GAPDH | GUSB | CD133/ GAPDH | CD133/ GUSB | CD133/ GAPDH | CD133/ GUSB |
| CASES | | | | | | | |
| A111-01* | 4.58E+01 | 3.20E+05 | 6.70E+03 | 1.43E−04 | 6.84E−03 | 1.43E−02 | 6.84E−01 |
| A101-01* | 5.87E+01 | 7.00E+05 | 2.44E+04 | 8.39E−05 | 2.41E−03 | 8.39E−03 | 2.41E−01 |
| A105-01* | 2.66E+01 | 4.38E+05 | 9.89E+03 | 6.07E−05 | 2.69E−03 | 6.07E−03 | 2.69E−01 |
| A102-01* | 8.39E+00 | 1.79E+05 | 5.79E+03 | 4.69E−05 | 1.45E−03 | 4.69E−03 | 1.45E−01 |
| A104-01* | 2.32E+01 | 2.16E+05 | 7.03E+03 | 1.07E−04 | 3.30E−03 | 1.07E−02 | 3.30E−01 |
| AVG | | | | 8.84E−05 | 3.34E−03 | 8.84E−03 | 3.34E−01 |
| CONTROLS | | | | | | | |
| 3 | 1.08E+02 | 3.62E+05 | 7.92E+03 | 2.98E−04 | 1.36E−02 | 2.98E−02 | 1.36E+00 |
| 4 | 5.13E+01 | 2.89E+05 | 4.03E+03 | 1.78E−04 | 1.27E−02 | 1.78E−02 | 1.27E+00 |
| 6 | 1.40E+02 | 2.57E+05 | 6.73E+03 | 5.45E−04 | 2.08E−02 | 5.45E−02 | 2.08E+00 |
| 8 | 1.00E+02 | 2.98E+05 | 8.79E+03 | 3.36E−04 | 1.14E−02 | 3.36E−02 | 1.14E+00 |
| 9 | 8.48E+01 | 3.75E+05 | 1.35E+04 | 2.26E−04 | 6.28E−03 | 2.26E−02 | 6.28E−01 |
| AVG | | | | 3.16E−04 | 1.30E−02 | 3.16E−02 | 1.30E+00 |
| POS CONTROLS | | | | | | | |
| POS HI | 1.41E+04 | 3.00E+05 | 1.99E+03 | 4.70E−02 | 7.09E+00 | 4.70E+00 | 7.09E+02 |
| POS LO | 6.73E+01 | 3.26E+03 | 7.21E+00 | 2.06E−02 | 9.33E+00 | 2.06E+00 | 9.33E+02 |
| AVG | | | | 3.38E−02 | 8.21E+00 | 3.38E+00 | 8.21E+02 |

*indicated patients showing a complete response to XCEL therapy (e.g., remained disease-free after an extended period of time).
Controls indicate samples from cancer0free control subjects;
"POS HI" and "POS LO" indicate patient that showed cancer recurrence and segriated into two populations with relatively high CD 133 and relatively low CD 133, respectively.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,966,891
U.S. Pat. No. 5,279,721
U.S. Pat. No. 8,044,033
NM_001145847.1
NM_001145848.1
NM_001145849.1
NM_001145850.1
NM_001145851.1
NM_001145852.1
NM_006017.2
Abdalla et al., *Ann. Surg.*, 239:818-825, 2004.
Abushullaih et al., *Cancer Invest.*, 20:3-10, 2002.
Adam et al., *Ann. Surg. Oncol.*, 8:347-353, 2001.
Altorki et al., *Clin. Cancer Res.*, 11:4191-4197, 2005.
Ausubel et al., *Current Protocols in Molecular Biology*, Greene Publishing Associates and Wiley Interscience, N.Y., 1998.
Ausubel, *Current Protocols in Molecular Biology*, Greene Publishing Associates and Wiley Interscience, N.Y., 1996.
Becerra et al., *Int. J. Cancer*, 105:868-872, 2003.
Ben-Josef et al., *J. Clin. Oncol.*, 23:8739-8747, 2005.
Bertolini et al., *Cancer Res.*, 63:4342-4346, 2003.
Blanquicett et al., *Clin. Cancer Res.*, 11:8773-8781, 2005.
Bolin et al., *Ann. Surg.*, 198:151-158, 1983.
Browder et al., *Cancer Res.*, 60:1878-1886, 2000.
Cianchi et al., *Gastroenterology*, 121:1339-1347, 2001.
Cunningham et al., *N Engl. J. Med.*, 351:337-345, 2004.
Dawson et al., *J. Clin. Oncol.*, 18:2210-2218, 2000.
De Jager et al., *Semin. Nucl. Med.*, 23(2):165-179, 1993.
Demetri et al., *Proc. Am. Soc. Clin. Oncol.*, 23:308, 2005.
Díaz Rubio et al., *Proc. Am. Soc. Clin. Oncol.*, 23(16s)3535, 2005.
Doolittle and Ben-Zeev, *Methods Mol, Biol*, 109:215-237, 1999.
Douillard et al., *Lancet.*, 355:1041-1047, 2000.
El-Rayes et al., *Proc. Am. Soc. Clin. Oncol.*, 23(308):3677, 2005.
Escudier et al., *Proc. Am. Soc. Clin. Oncol.*, 23(380):4510, 2005.
Fingl et al., In: *The Pharmacological Basis of Therapeutics*, 1:1, 1975.
Fong et al., *Ann. Surg.*, 230:309-318, 1999.
Fong, *Adv. Surg.*, 34:351-381, 2000. Furstenberger et al., *Br. J. Cancer*, 94(4):524-531, 2006.
Giantonio et al., *Proc. Am. Soc. Clin. Oncol.*, 23(16s):2, 2005.
Goldberg et al., *J. Clin. Oncol.*, 22:23-30, 2004.
Goldstein et al., *Am. J. Gastro.*, 95:1681-169, 2000.
Grothey et al., *J. Clin. Oncol.*, 22:1209-1214, 2004.
Gulbis and Galand, *Hum. Pathol.* 24(12), 1271-1285, 1993.
Hill et al., *N Engl. J. Med.*, 348:593-600, 2003.
Hobson and Denekamp, *Br. J. Cancer*, 49:405-413, 1984.
Hochster, *Semin. Oncol.*, 33:S8-14, 2006
Hoff et al., *J. Clin. Oncol.*, 22:2078-2083, 2004.
Hoff et al., *J. Clin. Oncol.*, 9:2282-2292, 2001.
Hurwitz et al., *N Engl. J. Med.*, 350:2335-2342, 2004.
Iinuma et al., *J. Clin. Oncol.*, 29(12):1547-1555, 2011
Janjan et al., *Int. J. Radiation Biol. Phys.*, 47:713-718, 2000.
Jemal et al., *CA Cancer J. Clin.*, 55:10-30, 2005.
Kang et al., *J. Am. Soc. Nephrol.*, 13:806-816, 2002.
Kemeny et al., *N Engl. J. Med.*, 341:2039-2048, 1999.
Kerbel and Kamen, *Nat. Rev. Cancer*, 6:423-436, 2004.
Kieran et al., *J. Pediatr. Hematol. Oncol.*, 27:573-581, 2005.
Kim et al., *Int. J. Radiat. Oncol. Biol. Phys.*, 63(2):346-353. 2005.
Lee et al., *Jpn. J. Clin. Oncol.*, 34:400-404, 2004.
Lin et al., *AACR*, Abstract #1342, 2002.
Lin et al., *Oncology*, 16s:31-37, 2002.
Lin et al., *Proc. Am. Soc. Clin. Oncol.*, 23:269, 2005.
Lyden et al., *Nat. Med.*, 7(11):1194-1201, 2001.
Ma et al., *Proc. Natl. Acad. Sci. USA*, 99:13243-13247, 2002.
Mancuso et al., *Pathophysiol. Haemost. Thromb.*, 33:503-506, 2003.
Masferrer et al., *Cancer Res.*, 60:1306-1311, 2000.
Mercer et al., *Anticancer Drugs*, 16:495-500, 2005.
Milas, *Am. J. Clin. Oncol.*, 26(4):S66-S69, 2003.
Nagore et al., *Am. J. Clin. Dermatol.*, 1:225-234, 2000.
Nakamura et al., In: *Handbook of Experimental Immunology* (4$^{th}$ Ed.), Weir et al. (Eds.), 1:27, Blackwell Scientific Publ., Oxford, 1987.
O'Reilly et al., *Cell*, 88:277-285, 1997.
O'Reilly et al., *Nat. Med.*, 2:689-692, 1996.
Patt et al., *Proc. Am. Soc. Clin. Oncol.*, 22(15s):3602, 2004.
Peichev et al., *Blood*, 95:952-958, 2000.
Remington's Pharmaceutical Sciences, 18th Ed. Mack Printing Company, pp. 1289-1329, 1990.
Rothenberg et al., *J. Clin. Oncol.*, 21:2059-2069, 2003.
Sambrook et al., In: *Molecular cloning: a laboratory manual*, 2$^{nd}$ Ed., Cold Spring Harbor Laboratory Press, Cold Spring Harbor, N.Y., 1989.
Shaked et al., *Blood*, 106:3058-3061, 2005.
Sheng et al., *Cancer Res.*, 58:362-366, 1998.
Solomon et al., *N Engl. J. Med.*, 352:1071-1080, 2005.
Spieth et al., *Cancer Chemother. Pharmacol.*, 52:377-382, 2003.
Sussman et al., *Cancer Biol. Therapy*, 2:255-256, 2003.
Taieb et al., *J. Clin. Oncol.*, 23:502-509, 2005.
Topham and Adam, *Semin. Oncol.*, 29:3-10, 2002.
Topol, *JAMA*, 293:366-368, 2005.
Tournigand et al., *J. Clin. Oncol.*, 22:229-237, 2004.
Van Cutsem et al., *J. Clin. Oncol.*, 19:4097-4106, 2001.
Werner et al., *N Engl. J. Med.*, 353:999-1007, 2005.
Willett et al., *Nat. Med.*, 10:145-147, 2004.

The invention claimed is:

1. An in vitro method for determining a complete response to an anti-cancer therapy in a subject comprising:
   (a) determining a CD133 RNA expression level in a biological sample of a subject who has undergone or is undergoing an anticancer therapy to treat colorectal cancer comprising administration of a fluorocytidine derivative and a COX-2 enzyme inhibitor; and
   (b) identifying the subject as having a complete response to the anticancer therapy if the CD133 RNA expression level in the sample is (i) less than about 0.56, when normalized to GAPDH RNA level, or (ii) less than the CD133 RNA expression level in a sample from a cancer-free control.

2. An in vitro method of detecting a biomarker of cancer stem cells in a subject comprising:
   (a) determining CD133 RNA expression level in a biological sample of a subject who has undergone or is undergoing an anticancer therapy to treat colorectal cancer comprising administration of a fluorocytidine derivative and a COX-2 enzyme inhibitor; and
   (b) identifying the subject as having a biomarker of cancer stem cells if the CD133 RNA expression level in the sample is greater than about 0.56, when normalized to GAPDH RNA level.

3. A method for treating a subject comprising:
   a) selecting a subject that has received or is receiving an anticancer therapy to treat colorectal cancer comprising administration of a fluorocytidine derivative and a COX-2 enzyme inhibitor and determined to have a CD133 RNA expression level (i) greater than about 0.56, when normalized to GAPDH RNA level; or (ii) greater than the CD133 RNA expression level in a sample from a cancer-free control; and
   b) administering a further anticancer therapy to the subject.

4. The method of claim 3, wherein the further anticancer therapy comprises treatment with a fluorocytidine derivative and a COX-2 enzyme inhibitor.

5. The method of claim 3, wherein the further anticancer therapy comprises radiation therapy, chemotherapy, immunotherapy or surgery.

6. The method of claim 3, wherein selecting a subject comprises measuring the CD133 RNA expression level for the subject.

7. The method of claim 3, comprising selecting a subject determined to have a CD133 RNA expression level greater than about 0.56, when normalized to GAPDH RNA level.

8. The method of claim 7, comprising selecting a subject determined to have a CD133 RNA expression level between about 0.56 and 7.0, when normalized to GAPDH RNA level.

9. The method of claim 3, comprising selecting a subject determined to have a CD133 RNA expression level greater than the CD133 RNA expression level in a sample from a cancer-free control.

10. The method of claim 9, comprising selecting a subject determined to have a CD133 RNA expression level less than 10 times higher than the CD133 RNA expression level in a sample from a cancer-free control.

11. The method of claim 3, wherein the cancer-free control is an age-matched control.

12. The method of claim 3, wherein the colorectal cancer is a metastatic colorectal cancer.

13. The method of claim 3, wherein the colorectal cancer is a metastatic colorectal cancer with nodal metastases.

14. The method of claim 3, wherein the fluorocytidine derivative is capecitabine.

15. The method of claim 3, wherein the COX-2 enzyme inhibitor is meloxicam, valdecoxib, celecoxib, rofecoxib or naproxen.

16. The method of claim 15, wherein the COX-2 enzyme inhibitor is celecoxib.

17. The method of claim 3, wherein the subject is further determined to have an elevated expression level of CEA, CK19 or CK20 relative to a control level.

* * * * *